(12) United States Patent
Yazaki et al.

(10) Patent No.: US 6,580,005 B1
(45) Date of Patent: Jun. 17, 2003

(54) PROCESS FOR RECOVERING TEREPHTHALIC ACID FROM PULVERIZED PRODUCT OF SPENT POLYETHYLENE TEREPHTHALATE AND SYSTEM FOR USE IN SUCH PROCESS

(75) Inventors: Jinichi Yazaki, Omiya (JP); Kozaburo Sakano, Yokohama (JP); Nobuyuki Funakoshi, Tokyo (JP); Kazuho Tanaka, Tokyo (JP)

(73) Assignee: Tsukishima Kikai Co., Ltd., Tokyo (JP)

( * ) Notice: Subject to any disclaimer, the term of this patent is extended or adjusted under 35 U.S.C. 154(b) by 0 days.

(21) Appl. No.: 09/721,057

(22) Filed: Nov. 22, 2000

(30) Foreign Application Priority Data

Nov. 26, 1999 (JP) ............................... 11-335908

(51) Int. Cl.$^7$ ............................... C07C 51/09
(52) U.S. Cl. ..................... 562/483; 562/485; 562/486
(58) Field of Search ................ 562/483, 486, 562/485

(56) References Cited

U.S. PATENT DOCUMENTS

| | | | |
|---|---|---|---|
| 4,542,239 A | * | 9/1985 | Lamparter et al. |
| 4,755,295 A | * | 7/1988 | Donhauser et al. |
| 5,502,247 A | * | 3/1996 | Bartos et al. |
| 6,075,163 A | * | 6/2000 | Roh et al. |

FOREIGN PATENT DOCUMENTS

JP          09286744 A   * 11/1997

OTHER PUBLICATIONS

Aldrich Handbook of Fine Chemicals, 1998–1999, p. 766.*

* cited by examiner

Primary Examiner—Rosalynd Keys
(74) Attorney, Agent, or Firm—Koda & Androlia

(57) ABSTRACT

This invention provides a process a process for recovering terephthalic acid from pulverized products of spent polyethylene terephthalate. This process comprises (1) a decomposition reaction step where the pulverized products of spent polyethylene terephthalate are continuously subjected to decomposition reaction in ethylene glycol in the presence of alkali, which is equimolar or excessmolar relative to the polyethylene terephthalate, so that salt of terephthalic acid and ethylene glycol can be continuously obtained; (2) a solid-liquid separation, dissolution, impurities-removing step where the ethylene glycol is separated from decomposition reaction slurry of salt of terephthalic acid and ethylene glycol, and the solid salt of terephthalic acid is dissolved into water, while insoluble impurities are removed; (3) a neutralization, crystallization step, where solution of said salt of terephthalic acid is neutralized with acid so that terephthalic acid can be crystallized; (4) a solid-liquid separation, washing step where slurry of terephthalic acid crystals is subjected to solid-liquid separation so that the terephthalic acid crystals can be obtained and washed; and (5) a drying, pulverization step where the washed terephthalic acid crystals are dried and pulverized.

7 Claims, 18 Drawing Sheets

SOLUTION OF SALT OF TEREPHTHALIC ACID

PROCESS FOR RECOVERING TEREPHTHALIC ACID FROM PULVERIZED PRODUCT OF SPENT POLYETHYLENE TEREPHTHALATE AND SYSTEM FOR USE IN SUCH PROCESS

DETAILED DESCRIPTION OF THE INVENTION

1. Field of the Invention

This invention relates to a process for technically recovering terephthalic acid as the material of polyethylene terephthalate (PET), from spent PET, which is used as bottles containing beverages and the like and also to a system for use in such process.

2. Background of the Invention

Several methods have been proposed in each of which, PET is decomposed for recovering monomer components therefrom, and thus recovered monomer components can be used as the material of PET. Among these conventional methods, typical ones are listed below.

(1) Methanolysis method where depolymerization is carried out for PET with methanol in vapor phase or liquid phase for producing dimethyl terephthalate;

(2) Glycolysis method where depolymerization is carried out for PET with ethylene glycol for utilizing an intermediate product, i.e., bis hydroxyethyl terephthalate as the, material of polymer; or Ester interchange method where dimethyl terephthalate is obtained from the product of the Glycolysis method, i.e., bis hydroxyethyl terephthalate with methanol; and (3) Hydrolysis method where hydrolysis is carried out for PET with alkali solution so that the resulting metallic salt terephthalate is neutralized with acid for the crystallization of terephthalic acid.

However, the above methods have drawbacks respectively.

In the method (1) (Methanolysis method), its reaction temperature is so low of about 177° C., which requires a lot of reaction time.

The method (2) (Glycolysis method), like the method (1) (Methanolysis method), also requires a lot of reaction time. Additionally, it is difficult to depolymerize perfectly to recover the monomer components. Further, the intermediate product, i.e., bis hydroxyethyl terephthalate is partly dissolved into the ethylene glycol. Then, it is difficult to separate the dissolved bis hydroxyethyl terephthalate from the ethylene glycol, which results in poor yield.

In the method (2) (Ester interchange method), it is difficult to separate the ethylene glycol from the methanol. Further, since the dimethyl terephthalate is partly dissolved into the methanol, it is also difficult to separate the dissolved dimethyl terephthalate from the methanol.

In the method (3) (Hydrolysis method), it is more difficult to produce the terephthalic acid than the case of bis hydroxyethyl terephthalate and the case of dimethyl terephthalate. Further, the recovered terephthalic acid might be contaminated with various additives contained in the spent PET, which results in a problem.

To cope with the above problems, Japanese Published Unexamined Patent Application No. 286744/97 proposes a method, in which PET is decomposed with alkali in ethylene glycol.

However, the method disclosed in this patent publication has a problem because the terephthalic acid is not sufficiently recovered. Therefore, it is necessary to attain a method for recovering a polymer having high purity. Additionally, since these conventional methods are performed in pilot scales, there is an increased demand for establishment of practical and technical process of this kind.

SUMMARY OF THE INVENTION

It is therefore, the object of the present invention is to provide a technical and practical process of this kind with high recovery of terephthalic acid. The other objects of the present invention will be clear from the following explanation.

In accordance with the first aspect of the present invention, there is provided a process for recovering terephthalic acid from pulverized products of spent polyethylene terephthalate, the process comprising the following steps;

(1) a decomposition reaction step where the pulverized products of spent polyethylene terephthalate arm continuously subjected to decomposition reaction in ethylene glycol in the presence of alkali, which is equimolar or excessmolar relative to the polyethylene terephthalate, so that salt of terephthalic acid and ethylene glycol can be obtained;

(2) a solid-liquid separation, dissolution, impurities-removing step where the ethylene glycol is separated from decomposition reaction slurry of the salt of terephthalic acid and ethylene glycol, and the solid salt of terephthalic acid is dissolved into water and insoluble impurities are removed;

(3) a neutralization, crystallization step, where the resulting solution of salt of terephthalic acid is neutralized with acid so that terephthalic acid can be crystallized;

(4) a solid-liquid separation, washing step where the resulting slurr of terephthalic acid crystals is subjected to solid-liquid separation so that the terephthalic acid crystals can be obtained and washed; and (5) a drying, pulverization step where the washed terephthalic acid crystals are dried and pulverized.

According to the first aspect of the present invention, the terephthalic acid having high purity can be technically recovered with high efficiency from the pulverized products of spent polyethylene terephthalate.

The alkali comprising mainly sodium carbonate can be used as the above alkali and sulfuric acid can be used as the above acid. Due to the alkali comprising mainly the sodium carbonate, carbon dioxide is generated by the decomposition reaction, thus inlet gas is not required. Further when the sulfuric acid is used as the acid, the sodium sulfate (mirabilite) can be crystallized by the neutralization and recovered.

Water contained in liquid obtained by separation in the step (4) (the solid-liquid separation, washing step) is vaporized so that the sodium sulfate can be crystallized and separated. The resulting steam is condensed for re-using as the water for dissolving the salt of terephthalic acid, whereby the amount of required water can be decreased.

In the step (2) (solid-liquid separation, dissolution, impurities-removing step), by utilizing a crossfeed belt type vacuum filtering dissolver, the separation of the ethylene glycol, the dissolving of the solid salt of terephthalic acid, and the removing of the insoluble impurities can be continuously carried out.

The process in accordance with the first aspect of the present invention might further comprise the following steps:

(6) a return step where the ethylene glycol, which is obtained by the solid-liquid separation in the above step (2) (solid-liquid separation, dissolution, impurities-removing step) is returned to the step (1) (decomposition reaction step); and (7) a vaporization, crystallization, separation, return step where water contained in separation liquid obtained from the step (4) (the solid-liquid separation, washing step) is vaporized so that the salt can be crystallized and separated, then the reminder, i.e., the ethylene glycol is returned to the step (1) (decomposition reaction step).

By returning the ethylene glycol, the amount of required ethylene glycol can be decreased.

The process in accordance with the first aspect of the present invention might further comprise, between the step (2) (solid-liquid separation, dissolution, impurities-removing step) and step (3) (neutralization, crystallization step), the following step;

(8) soluble impurities-removing step where soluble impurities, which are contained in solution in the above step (2), can be continuously removed with an adsorbent packed adsorber.

As water used for the dissolution in the above step (2), wash water of the adsorber in the step (8) and/or condensate obtained by cooling steam in the step (7) can be re-used for saving water.

Between the above step (1) (decomposition reaction step) and step (2) (solid-liquid separation, dissolution, impurities-removing step), the decomposition reaction slurry can be passed through orifice means. Due to this orifice means, the ethylene glycol can be partly prevented from being passed to the step (2). This means that the slurry having small amount of ethylene glycol is passed to the step (2). Accordingly, load applied to the step (2) can be lowered.

The above orifice means might comprise: a tapered cylinder and a screw conveyor placed in the cylinder. The orifice means of this kind can be easily formed by providing tapered cylinder and the screw conveyor placed in an outlet portion of a screw press.

In the above step (1) (decomposition reaction step), a horizontal type decomposition reactor can be used. This reactor comprises: a cylinder, which has a body portion and a tapered portion connected to the fore end portion of the body portion; and a screw conveyor, which is placed in the cylinder and which has a tapered portion corresponding to the above tapered portion of the cylinder. Then, the pulverized products of spent polyethylene terephthalate, ethylene glycol, and alkali are charged into the above horizontal type decomposition reactor. In this reactor, the ingredients are subjected to the decomposition reaction, mainly in the body portion, so that the salt of terephthalic acid and the ethylene glycol can be obtained. Finally, the resulting decomposition reaction slurry can be extruded from the tapered portion of the cylinder.

For the neutralization of the step (3) (neutralization, crystallization step), the above solution of salt of terephthalic acid can be fed into a neutralization chamber, where the solution is subjected to acid jetting. Then, acid jetting point is moved peripherally with the passage of time. By such movement of jetting point, the neutralization can be promoted in the neutralization chamber, which enables complete neutralization while any unreacted acid is not remained.

For the neutralization of the step (3) (neutralization, crystallization step), ultrasonic vibration can be applied in the neutralization chamber. Also due to the ultrasonic vibration, the neutralization can be promoted, which enables complete neutralization while any unreacted acid is not remained.

For the drying of the step (5) (drying, pulverization step), indirect heating is performed by heating medium passing through a jacket and/or an agitating blade means under reduced pressure of inside of a container for the drying. By drying the terephthalic acid crystals in this way, the degeneration of terephthalic add can be prevented, and the terephthalic acid crystals can be dried in short time.

For the washing of the step (4) (solid-liquid separation, washing step), the slurry of terephthalic acid crystals is supplied to a running filter cloth. Then, this filter cloth is divided into a plurality of filtering and washing zones along the running direction of the filter cloth. In one filtering and washing zone, wash water is sprayed and the slurry is filtered by vacuum suction so that filtrate is obtained under this filtering and washing zone. This filtrate is used as a wash water in another filtering and washing zone located at the upstream side of the above filtering and washing zone, that is to say, counter-flow type washing is carried out. In this embodiment, the filtering and washing can be performed efficiently.

In accordance with the second aspect of the present invention, there is provided a process for recovering terephthalic acid from pulverized products of spent polyethylene terephthalate, the process comprising the following steps;

(1) a decomposition reaction step where the pulverized products of spent polyethylene terephthalate are subjected to decomposition reaction in ethylene glycol in the presence of alkali, which is equimolar or excess-molar relative to the polyethylene terephthalate, so that salt of terephthalic acid and ethylene glycol can be obtained;

(2) a solid-liquid separation step where the ethylene glycol is separated from decomposition reaction slurry of the salt of terephthalic acid and the ethylene glycol;

(3) a dissolution step where the salt of terephthalic acid, which is obtained by separating ethylene glycol from the slurry, is dissolved into water;

(4) a neutralization, crystallization step where the resulting solution of salt of terephthalic acid is neutralized with acid so that terephthalic acid can be crystallized;

(5) a solid-liquid separation, washing step where the slurry of terephthalic acid crystals is subjected to solid-liquid separation so that the terephthalic acid crystals can be obtained and washed; and (6) a drying, pulverization step where the washed terephthalic acid crystals are dried and pulverized.

As shown in the second aspect of the present invention, even if the step (2) (solid-liquid separation step) and the step (3) (dissolution step) are performed separately, the directing terephthalic acid can be obtained smoothly.

In the above step (1) (decomposition reaction step), a vertical type stirring vessel can be used for the decomposition reaction. When operation is passed from the step (1) to the step (2), the decomposition reaction slurry can be passed through a vertical type orifice means. This orifice means comprises a tapered cylinder and a screw conveyor placed in this cylinder. Due to this orifice means, the ethylene glycol can be partly prevented from being passed to the step (2). On the other hand, the ethylene glycol can be returned to the stirring vessel from the larger diameter side of the above cylinder. Thus, the slurry containing small amount of ethylene glycol can be passed to the step (2). Accordingly, load applied to the step (2) can be lowered.

In accordance with the third aspect of the present invention, there is provided a process comprising a decomposition reaction step where pulverized products of spent polyethylene terephthalate are subjected to decomposition reaction in solvent in the presence of alkali, which is equimolar or excessmolar relative to the polyethylene terephthalate, so that salt of terephthalic acid and ethylene glycol can be obtained, for recovering terephthalic acid from the resulting salt of terephthalic acid, and the above decomposition reaction step being constructed from equal to or more than two stages, i.e., multiple stages.

The pulverized products of spent PET are formed by crushing PET bottles or the like. Then, each PET article of this kind has many parts made of different materials, thus time required for decomposition reaction is different for each part. Accordingly, in order to decompose completely the pulverized products of spent PET, it takes time long enough to decompose a part where the decomposition reaction is slowest among all the parts. Precisely, even after the decomposition reaction is completed at a certain part, this process can not move to next step as long as decomposition reaction is occurred at any part. This causes low efficiency.

In this connection, in the third aspect of the present invention, since the decomposition reaction step is constructed from equal to or more than two stages, i.e., multiple stages, the decomposition reactions in the parts of the pulverized products are performed in corresponding stages, respectively, so that the reactions in these all parts ran be finished simultaneously, resulting in improved efficiency of the process.

As one embodiment in accordance with this aspect of the present invention, the above decomposition reaction step might comprise two stages; a previous heating stage and a decomposition reaction heating stage. In the previous heating stage, the above pulverized products are previously heated for 5 minutes or more at the temperature range from 100° C. to the temperature at which the decomposition reaction of the above pulverized products is not substantially started. On the other hand, in the decomposition reaction heating stage, the above pulverized products are subjected to the decomposition reaction at the temperature range from the temperature at which the decomposition reaction of the above pulverized products is substantially started and the boiling point of the solvent.

As the solvent, ethylene glycol can be used and the above pious heating can be performed at the temperature of 100 to 140° C., while the above decomposition reaction can be performed at the temperature of 130 to 180° C.

As stated above, as for the previous beating stage, where the above pulverized products are previously heated for 5 minutes or more at the temperature range from 100° C. to the temperature at which the decomposition reaction of the above pulverized products is not substantially started, and as for the decomposition reaction heating stage where the above pulverized products are subjected to the decomposition reaction at the temperature range from the temperature at which the decomposition reaction of the above pulverized products is substantially started to the boiling point of the solvent, particularly, if the ethylene glycol is used as the solvent, the above previous heating temperature is 100 to 140° C., while the above decomposition reaction temperature is 130 to 180° C. By performing the previous heating before the decomposition reaction, the amorphous pars of the pulverized products of spent PET are crystallized and subjected easily to the decomposition reaction. As a result, the decomposition reactions in these all parts can be finished simultaneously, resulting in improved efficiency of the process in the decomposition reaction stage.

Further, before the previous heating stage, impurities, each of which has smaller specific gravity than that of the solvent, are preferably removed.

Generally, tee pulverized products of spent PET contain impurities such as polypropylene (PP) and polyethylene (PE). When the impurities are heated, they will surely melt. Hence, it is difficult, after heating, to remove such impurities. Then, if the impurities are not removed but remained, they will solidify when they are cooled. This might cause trouble in the other steps continuing after the decomposition reaction step. In order to avoid such trouble, it is preferable that the impurities such as PP and PE are removed before heating. Actually, the impurities float on the solvent such as ethylene glycol and water, because of smaller specific gravity than that of the solvent. Therefore, it is surely possible that the floating impurities are removed from the solvent before heating. Particularly, when the ethylene glycol is used as the solvent, such impurities can be removed easily, due to the large difference of specific gravity between the impurities and the ethylene glycol.

As a decomposition reactor used for a final stage of the above decomposition reaction step, a horizontal type decomposition reactor can be used. This reactor comprises: a cylinder, which has a body portion and a tapered portion connected to the fore end portion of the body portion; and a screw conveyor, which is placed in the cylinder and which has a tapered portion corresponding to the above tapered portion of the cylinder. Then, the pulverized products of spent polyethylene terephthalate, solvent, and alkali are charged into this horizontal type decomposition reactor. Continuously, the above pulverized products are subjected, mainly in the above body portion, to the decomposition reaction so that the salt of terephthalic acid and the ethylene glycol can be obtained. Finally, the resulting decomposition reaction slurry can be extruded from the tapered portion of the cylinder.

When the decomposition reaction slurry goes to the next step, since the slurry is extruded from the tapered portion as stated above, large amount of solvent is not required to be included in the slurry. Accordingly, the load applied to the next step can be lowered. Additionally, such extrusion is carried out continuously after the decomposition reaction in the horizontal type decomposition reactor. Therefore, any additional equipment for the extrusion is not required.

The sodium carbonate is preferably used as the alkali. Additionally, it is preferable that the mass ratio of the pulverized products of spent polyethylene terephthalate and the ethylene glycol is determined to be 1:0.8 to 1.2 in the previous heating and to be 1:2.0 to 2.5 in the decomposition heating.

When the sodium carbonate is used as the alkali, the pulverized products of spent PET are subjected to the decomposition reaction so that the sodium terephthalate and the ethylene glycol can be obtained. In this situation, the sodium terephthalate absorbs the ethylene glycol. Then, as stated above, in a certain part where the decomposition reaction is fast, even after the decomposition reaction of this part is completed, the reaction is continued due to the part where the decomposition reaction is slowest That is to say, after the decomposition reaction of this part is completed, sodium terephthalate continues to absorb the ethylene glycol as long as the decomposition reaction is occurred in other parts. This requires large amount of ethylene glycol.

In this connection, in the fourth aspect of the present invention, by provision of the previous heating, the decomposition reactions of the all parts of the pulverized products of spent PET can be finished simultaneously. Accordingly, the amount of ethylene glycol absorbed into the sodium terephthalate can be deceased. Then, if the mass ratio of the pulverized products of spent PET and the ethylene glycol is determined to be 1:0.8 to 1.2 in the previous heating, and it is determined to be 1:2.0 to 2.5 in the decomposition heating, the reactions can be carried out efficiently in both cases. As a result, the consumption of the ethylene glycol can be decreased. Here, the amount of ethylene glycol in the decomposition reaction heating refers to not the amount of ethylene glycol added in the decomposition reaction stage, but the total of the amount of ethylene glycol added in the previous heating stage and the amount of ethylene glycol added in the decomposition reaction stage.

In accordance with the fourth aspect of the present invention, there is provided a process comprising decomposition reaction heating carried out for the pulverized products of spent polyethylene terephthalate in solvent in is the presence of alkali, which is equimolar or excessmolar relative to the polyethylene terephthalate, so that salt of terephthalic acid and the solvent can be obtained, for recovering terephthalic acid from the resultant salt of terephthalic acid, and before the decomposition reaction, the above pulverized products are subjected to thermal degradation.

As stated above, each PET article such as PET bottle for beverage has many parts made of different materials, b, time required for decomposition reaction is different for each part. Accordingly, even after decomposition reaction is completed at a certain part, operation can not be passed to the next step as long as decomposition reaction is occurred at any part. In this connection, in accordance with the fourth aspect of the present invention, before the above decomposition reaction, the pulverized products of spent PET are subjected to thermal degradation so that the decomposition reactions in the all parts are finished simultaneously. Particularly, if this thermal degradation is performed at the temperature of 290 to 330° C. for more than 5 minutes, the amorphous parts of the pulverized products of spent PET are crystallized and subjected easily to the decomposition reaction As a result, the decomposition reaction can be finished quickly, resulting in high efficiency.

The thermal degradation can be carried out continuously and easily by utilizing a screw extruder.

Further, heat generated by the pulverized products subjected to the thermal degradation can be recycled for the decomposition reaction heating. This means that heat can be used efficiently, thereby efficient process can be attained. After the thermal degradation of the pulverized products, they are fed to the decomposition reaction step, where they are heated. Then, the amount of the fed pulverized products can be adjusted. By doing so, temperature control in this step is enabled.

In accordance with the fifth aspect of the present invention, there is provided a process for technically recovering terephthalic acid from pulverized products of spent polyethylene terephthalate. This process comprises: a thermal cracking course where the pulverized products of spent polyethylene terephthalate are subjected to thermal cracking in the presence of solvent and alkali so that salt of terephthalic acid and ethylene glycol can be obtained; and a removing course where the solvent is removed from thermal cracking slurry, by vaporizing the solvent under the atmospheric pressure or reduced pressure from the thermal cracking slurry, for recovering terephthalic acid from the resulting salt of terephthalic acid.

In order to remove the solvent from the thermal cracking slurry, i.e., to separate the thermal cracking slurry into the salt of terephthalic acid and the solvent, it is common that a filter or centrifugal separator is used. However, if such equipment is used, since the particles of the salt of terephthalic acid are very fine, the amount of the removed solvent can not be stable. Additionally, the removing operation takes long time. On the other hand, in this aspect of the present invention, the solvent is vaporized under the atmospheric pressure or reduced pressure. Accordingly, the amount of the removed solvent can be controlled freely and the removing operation can be carried out quickly.

Further, in this aspect of the present invention, there is provided a process for technically recovering terephthalic acid from pulverized products of spent polyethylene terephthalate. This process comprises: a thermal cracking course where the pulverized products of spent polyethylene terephthalate are subjected to thermal cracking in the presence of solvent and alkali so that the salt of terephthalic acid and ethylene glycol can be obtained; and a removing course where the solvent is removed from the thermal cracking slurry, by vaporizing the solvent under the atmospheric pressure or reduced pressure until the amount of the solvent contained in the solid salt of terephthalic acid is decreased to 20 to 30% by mass thereof, for recovering the terephthalic acid by dissolving the solid salt of terephthalic acid into water.

In this embodiment, the solvent and the ethylene glycol are removed from the solid salt of terephthalic add until the amount of the solvent contained in the solid salt of terephthalic acid is decreased to 20 to 30% by mass thereof. Therefore, the amount of water required to dissolve the solid salt of terephthalic can be decreased due to the certain amount of solvent contained in the solid salt of terephthalic acid.

To carry out the process according to this embodiment, there is provided a system recovering terephthalic acid from pulverized products of spent polyethylene terephthalate. This system comprises: a horizontal type decomposition reaction chamber; stirring means for stirring solvent, alkali, and the pulverized products of spent polyethylene terephthalate, which are charged into the decomposition reaction chamber; heating means for heating the same; a vacuum chamber, which is communicated with the upper portion of the above decomposition reaction chamber; and evacuating means, which is connected to the vacuum chamber. Then, in this system, the solvent contained in the above decomposition reaction chamber is removed through the above vacuum chamber, and the resulting solid salt of terephthalic acid will be used for recovering the terephthalic acid.

This system has the vacuum chamber, which is communicated with the upper portion of the decomposition reaction chamber, and evacuating means, which is connected to this vacuum chamber. Then, by forming a vacuum in the decomposition reaction chamber, the solvent can be vaporized. That is to say, the decomposition reaction chamber can be used not only for the decomposition reaction but also for the removing of solvent. Therefore, any additional equipment is not required for removing the solvent. Additionally, in this system, beat can be used efficiently.

In this aspect of the present invention, carbonate can be used as the alkali. When the carbonate is used as the alkali, carbon dioxide is generated the moment the decomposition reaction is started. Accordingly, the decomposition reaction chamber can be configured so as to be sealed internally by thus generated carbon dioxide. In this case, inert gas (e.g, nitrogen) is not required for this sealing.

Further, according to this embodiment, there is provided a system recovering terephthalic acid from pulverized products of spent polyethylene terephthalate. This system comprises: a decomposition reactor where the pulverized products of spent polyethylene terephthalate are subjected to thermal cracking in the presence of solvent and alkali so that salt of terephthalic acid and ethylene glycol can be obtained; an evaporator having a heating surface kept at the temperature equal to or higher than the boiling point of the above solvent; and falling means, by which the above thermal cracking slurry is fallen downward to the heating surface. Then, in this system, the solvent vaporized in the above evaporator is recovered axed returned to the above decomposition reactor.

In this system, by the falling means, the thermal cracking slurry of the salt of terephthalic acid and ethylene glycol can be brought into contact with the heating surface kept at the temperature equal to or higher than the boiling point of the above solvent, the solvent can be vaporized quickly. Further, the temperature of the heating surface can be adjusted so that the amount of removed solvent can be controlled freely.

In accordance with the sixth aspect of the present invention, there is provided a process for technically recovering terephthalic acid from pulverized products of spent polyethylene terephthalate. This process comprises: subjecting the pulverized products of spent polyethylene terephthalate to thermal cracking in the presence of alkali so that salt of terephthalic acid and ethylene glycol can be obtained; removing the ethylene glycol from thermal cracking slurry so that solid salt of terephthalic acid can be obtained; dissolving the solid salt of terephthalic acid into water so that solution of salt of terephthalic acid can be obtained; neutralizing this solution of salt of terephthalic acid by adding acid so that terephthalic acid can be crystallized and recovering the terephthalic acid. Then, in this process, the acid is added in multiple stages and the amount of added acid is determined so that the pH value of the solution in the final stage is adjusted to 2 to 4. Further, in this process, the terephthalic acid crystals obtained from the fin stage are returned to a previous stage and dissolved.

For crystallizing the terephthalic acid, it is usually considered that solution of salt of terephthalic acid is neutralized by adding acid until the pH value of the solution is adjusted to about 2. However, in this case, the particle size of each resulting terephthalic acid crystals is too small. To cope with this problem, there is provided a method where the acid is added to the solution of salt of terephthalic acid under high pressure at the temperature of 100 to 200° C. so that the terephthalic acid crystals each having large particle size can be obtained. However, this method makes the facility to be complicated, resulting in high cost. Further, since thus obtained terephthalic acid might form capillary crystals, the crystals tend to break. As a result, the terephthalic acid crystals each having the large particle size can not be obtained by the conventional methods.

On the other hand, according to the process of this aspect, the terephthalic acid crystals each having large particle size can be obtained at low cost.

It is preferable that the amount of added acid is determined so as not to crystallize the terephthalic acid in the proceeding stage.

It is also preferable that the acid is added in multiple stages while the amount of added acid is determined so that the pH value of the solution obtained from the final stage is adjusted to 2 to 4 and this solution is fed into a classifier so that classified terephthalic acid fine crystals are returned to a previous stage together with mother liquor. This embodiment ensures the terephthalic acid laving the large particle size.

It is possible that the solution containing the terephthalic acid crystals is subjected to solid-liquid separation so that the resulting terephthalic acid crystals are returned to the previous stage for dissolution again.

DESCRIPTION OF THE PREFERRED EMBODIMENT

The present invention will now be described in more detail below with reference to the preferred embodiments.

In the present invention, the pulverized products of spent polyethylene terephthalate are used as material. These pulverized are determined to include products formed by, for example, cutting, breaking or crushing spent PET such as collected PET bottle. Preferably, each pulverized product has the shape of 2 to 8 mm square. Then, as solvent, water, ethylene glycol (EG), propylene glycol (PG), silicone oil, and the like can be used. In the following embodiments, EG is used as the solvent.

The First Embodiment in Accordance with the First Aspect of the Present Invention FIGS. 1 to 4 and FIG. 6 illustrate the first embodiment in accordance with the first aspect of the present invention.

<Decomposition Reaction Staff>

Figure 2:
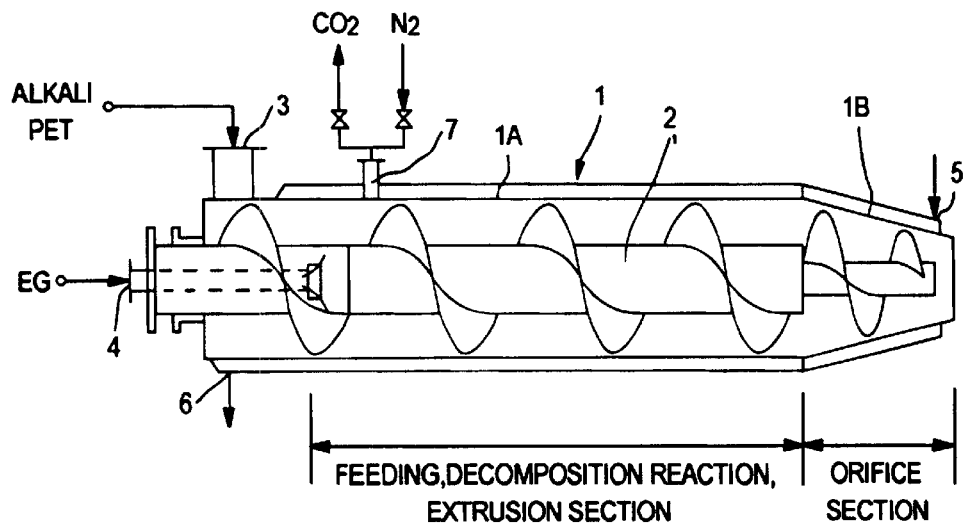
FIG. 2 is a conceptual illustration of a horizontal type decomposition reactor.
Figure 3:
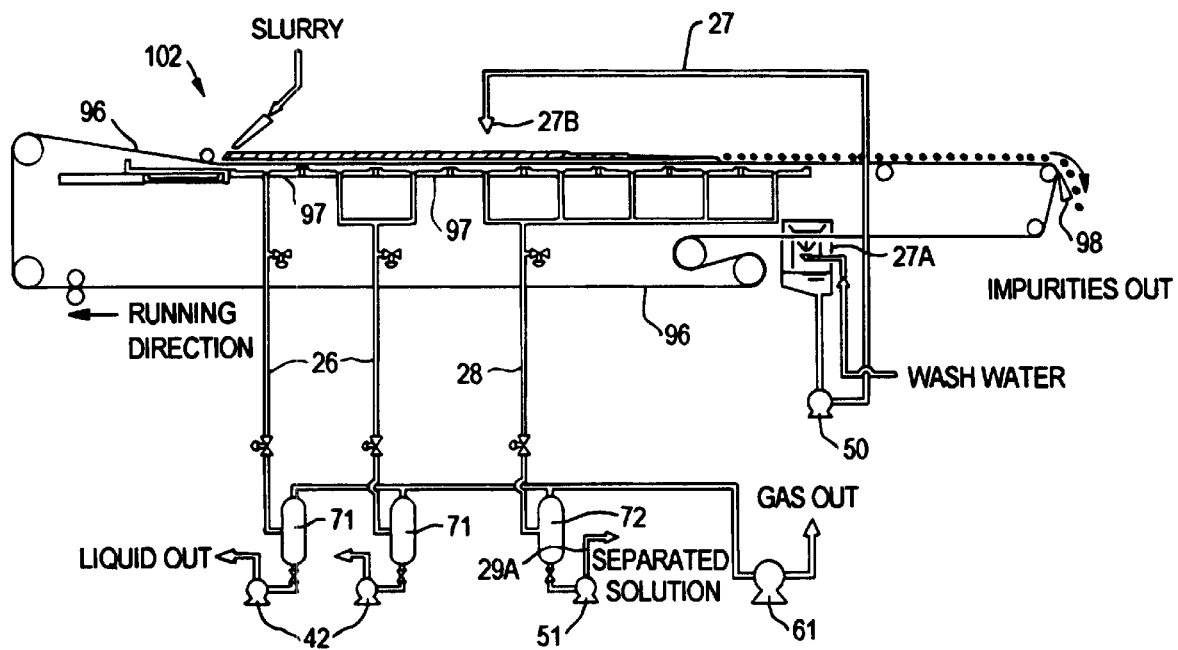
FIG. 3 is a conceptual illustration of a crossfeed belt type vacuum filtering dissolver.

Is used, for decomposition reaction in the present invention, a screw press type horizontal reactor exemplified closely in FIG. 2. This horizontal type decomposition reactor comprises a cylinder 1, which has a body portion 1A and a tapered portion 1B connected to the fore end portion of the body portion 1A; and a screw conveyor, which is placed in the cylinder 1 and which has a tapered portion corresponding to the above tapered portion 1B of the cylinder 1. The pulverized products of spent polyethylene terephthalate, alkali, which is equimolar or excessmolar relative to the polyethylene terephthalate, and ethylene glycol are charged into the above horizontal type decomposition reactor, where the decomposition reaction is carried out under the atmospheric pressure so that the salt of terephthalic acid and the ethylene glycol can be obtained mainly in the body portion 1A, and decomposition reaction slurry can be extruded from the tapered portion of the cylinder.

At the base of the body portion 1A, there is a charge inlet 3 through which the pulverized products of spent polyethylene terephthalate and the alkali are charged into the cylinder 1, while a shaft of the screw conveyor 2 serves as a charge inlet 4, through which the ethylene glycol is charged into as the cylinder 1. Then, a jacket is equipped to the external periphery of the cylinder 1 and on this jacket, there are inlet 5 and outlet 6 for beat medium.

The pulverized products of spent polyethylene terephthalate and the alkali are charged through the above charge inlet 3 into the cylinder 1, and the ethylene glycol are charged through the above charge inlet 4 into the cylinder 1. Then, in the body portion 1A, while the charged materials are fed toward the fore end portion by means of the screw conveyor 2, they are subjected to stirring operation so that the salt of terephthalic acid and ethylene glycol can be continuously obtained by decomposition reaction.

Then, the resulting decomposition reaction slurry is exuded from the tapered portion 1B. Accordingly, while the charged materials can be fed uniformly without back mixing, the slurry can be exuded from the tapered portion 1B.

As stated above, the cylinder 1 and the screw conveyor 2 are configured so as to have the tapered portions, respectively, whereby orifice means can be formed. Due to this orifice means, the amount of required ethylene glycol can be decreased. Further, the orifice means enables high effect of filtration in a next filtration step (solid-liquid separation step). Concretely, if the orifice means is not provided, the amount of ethylene glycol contained in the resulting decomposition reaction slurry is about 70%, while if the orifice means is provided, it can be reduced to about 30%

The alkali preferably comprises sodium carbonate as a main component and more preferably comprises 20% or less alkali metal hydroxide such as sodium hydroxide and potassium hydroxide. When the sodium hydroxide is contained, the efficiency of the decomposition reaction can be improved. Then, when the sodium carbonate is used as the main component of the charged alkali, carbon dioxide is generated the moment the decomposition reaction is started. In this case, any inert gas (e.g., nitrogen) is not required. Additionally, the sodium carbonate is cheap and about ½ the cost of sodium hydroxide.

The generated carbon dioxide is discharged through a gas passage 7 out of this system. On this gas passage 7, a selector valve is provided, which enables selection between the discharge of tile carbon dioxide and feeding of inert gas (e.g., nitrogen).

It is preferable that the alkali is previously brought into contact with the pulverized products of spent polyethylene terephthalate by means of direct spray or the like. By this treatment, the decomposition reaction time can be reduced to ⅕ to ⅛ at the decomposition reaction temperature of 120 to 190° C.

<Solid-Liquid Separation, Dissolution, Impurities-Removing Step>

Figure 1:
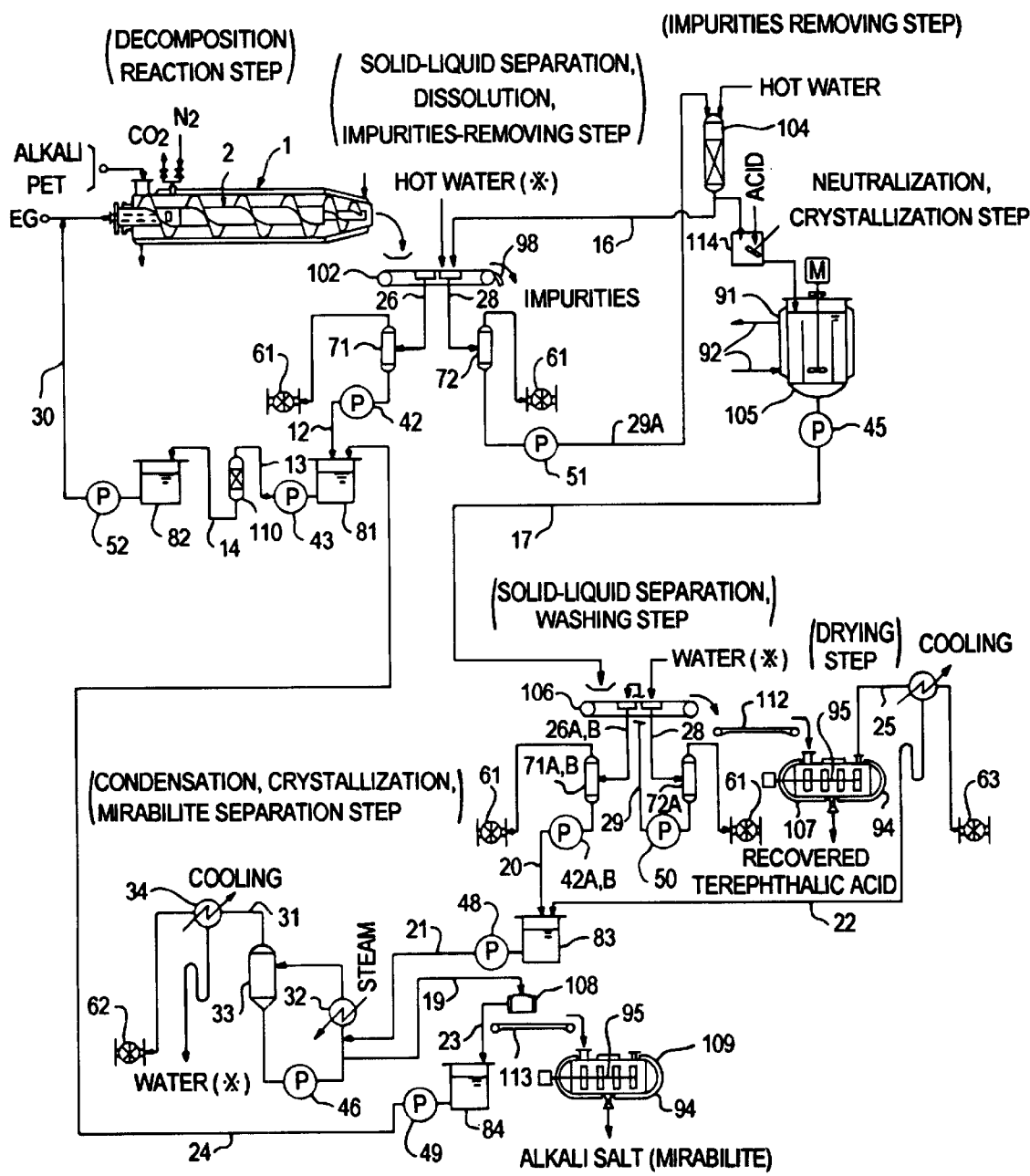
FIG. 1 is a flow diagram of the whole fist embodiment in accordance with the first aspect of the present invention.

The above decomposition reaction slurry of salt of terephthalic acid and ethylene glycol is passed, by means of pump, through a transport pipe to a solid-liquid separation, dissolution, impurities-removing apparatus. As this apparatus, there can be used a crossfeed belt type vacuum filtering dissolver 102, which is exemplified closely in FIG. 3 (the crossfeed belt type vacuum filtering dissolver of FIG. 1 is just a simplified illustration). In a filter section of the crossfeed belt type vacuum filtering dissolver 102, the ethylene glycol is separated from the decomposition reaction slurry. The detail explanation of this separation will be stated below. Alternatively, the separation can be carried out with another kind of separator, for example, a centrifugal separator.

The ethylene glycol contained in the decomposition reaction slurry is filtered by suction at a filtrate separator 71 by means of a vacuum pump 61. Filtrate is passed, by means of a pump 42, though a transport pipe 12 to a filtrate tank 81, and filtrate is collected there. Rough ethylene glycol collected in the filtrate tank 81 is, at a suitable time, passed, by means of a pump 43, through a transport pipe 13 to a purification column 110, where impurities are removed from the rough ethylene glycol. Alternatively, the impurities can be removed by distillation or membrane process.

The ethylene glycol, from which the impurities have been removed, is passed through a transport pipe 14 to a filtrate tank 82, and the ethylene glycol is collected there. The ethylene glycol collected in the filtrate tank 82 is, at a suitable time, passed, by means of a pump 52, through a transport pipe 30 to a screw press type horizontal reactor. Then, in this reactor, the ethylene glycol is reused as the material of the solvent for the decomposition reaction.

Even ethylene glycol, in which the impurities are remained, can be re-used as the material of the solvent for the decomposition reaction, within a scope where the impurity does not effect the purity of terephthalic acid. Further, part of the purified ethylene glycol can be reused as a material for producing PET.

The salt of terephthalic acid, which is recovered by separating the ethylene glycol from the decomposition reaction slurry, is continuously introduced into a dissolving section of the crossfeed belt type vacuum filter dissolver 102. Then, in this dissolving section, the terephthalic acid is dissolved into hot water, which is sprayed downward to this section. In this case, for example, the hot water is used 3 to 5 times as much as the terephthalic acid at the temperature of about 80° C. so that the solution of salt of terephthalic acid is obtained. It is possible to use, instead of this hot water, wash water of an adsorption column, water discharged from a solid-liquid separation, washing step, and condensate, which is obtained by cooling steam obtained from a condensation, crystallization, mirabilite-separation step. This adsorption column and these steps will be explained below.

The solution of salt of terephthalic acid is filtered by suction at a solution separator 72 by mean of a vacuum pump 61. The separated solution is passed, by means of a pump 51, through a pipe line 29A to a next soluble impurities-removing step.

In the crossfeed belt type vacuum filtering dissolver 102, at the downstream side end portion of a filter cloth 96, a scraper 98 is placed so as to be opposed to the running direction of the filter cloth so that the insoluble impurities can be removed.

<Impurities-Removing Step>

The solution of salt of terephthalic acid is passed, by means of the pump 51, through the pipe line 29A to the impurities-separator, e.g., a vertical type adsorptive active carbon packed cylindrical column 104. The flow rate of this solution is preferably 5 to 10 mm/m$^2$.min. In this separator, soluble impurities contained in the solution of salt of terephthalic acid can be adsorbed by the active carbon and removed. After adsorption, the active carbon in the separator 104 is washed with hot water. The used wash water is discharged from the separator 104 and is returned through the transport pipe 16 to the crossfeed belt type vacuum filtering dissolver 102. In this dissolver, the returned water can be re-used as a regenerative wash water. Further, it is preferable that, in order to remove pulverized coal, back wash is previously performed for granular coal or granulated coal. In this step, ion-exchange resin can be used instead of or additional to the active carbon. Alternatively, membrane process can be used for removing the impurities.

<Neutralization, Crystallization Step>

After the impurities-removing step, the solution of salt of terephthalic acid is neutralized with acid, e.g., sulfuric acid in a neutralization chamber 114 so that the pH value of the solution is adjusted to about 2 to 4. As the acid added to the solution, mineral acid suck as sulfuric acid, hydrochloric acid, phosphoric acid and nitric acid can be used. Particularly, the sulfuric acid is preferable.

In the neutralization chamber 114, it is required that the acid is stirred and mixed uniformly for ensuring the neutralization. Slurry of terephthalic acid crystals is formed by the neutralization and it is passed to a crystallization vessel 105 and collected there. This vessel 105 is defined by, for example, a vertical type cylindrical stirrer equipped with a jacket 91 on its external periphery, through which heat medium is passed.

In the neutralization vessel 114, the moment the acid is added, neutralization is started. Then, the terephthalic acid fine crystals are produced, at the same time, unreacted acid is included in an aggregate of the terephthalic acid fine crystals. After the neutralization, in the crystallization vessel 105, the included acid leaks from the aggregate, which might delays neutralization. As a result, the pH value can not be adjusted precisely and the terephthalic acid can not be produced reliably because of such unstable neutralization.

Figure 4:
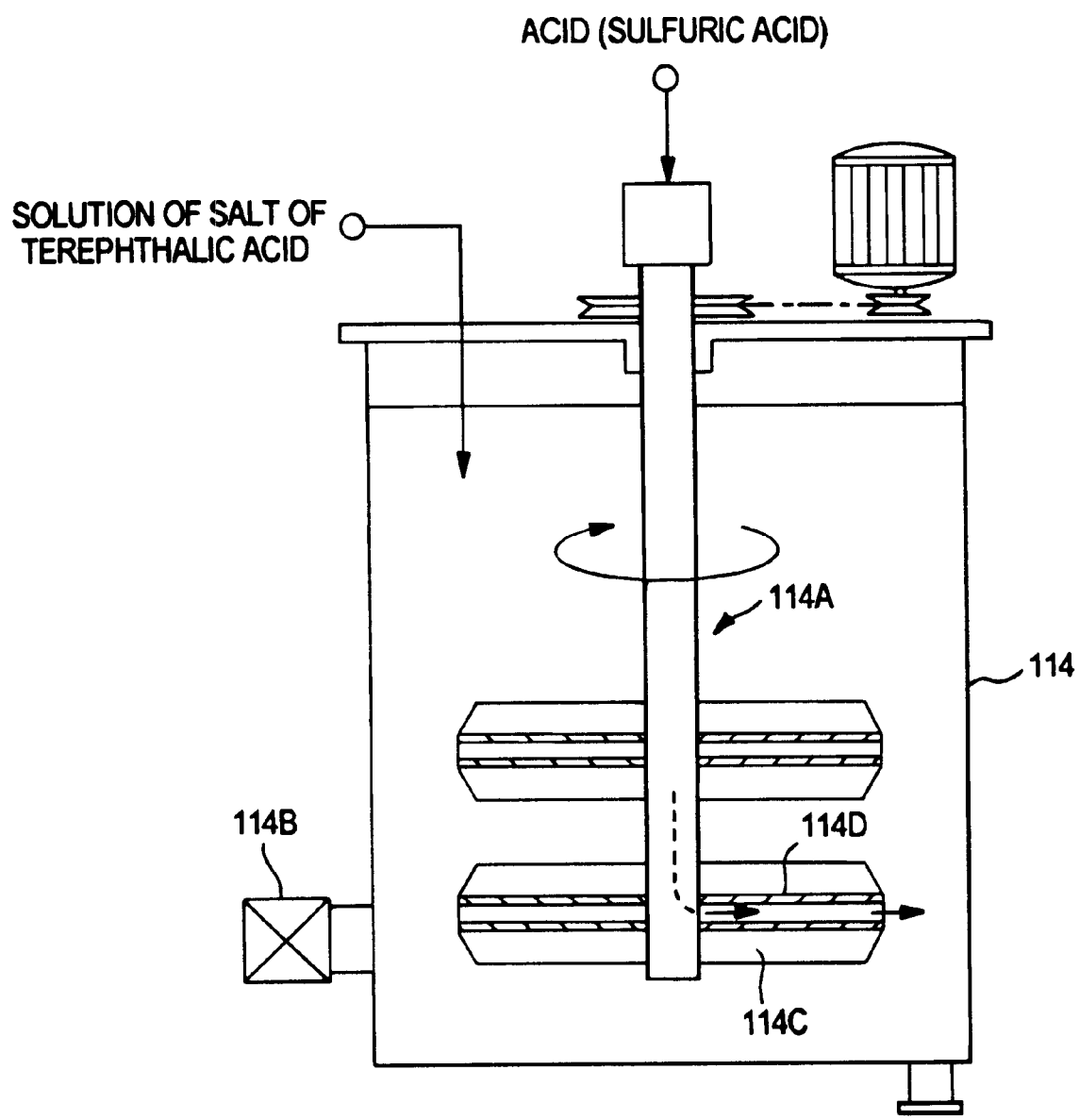
FIG. 4 is a schematic illustration of a structural embodiment of a neutralization chamber.

To cope with this problem, as shown in FIG. 4, an ultrasonic generator 114B is equipped to the neutralization vessel 114. Then, in this vessel 114, while the slurry of the terephthalic acid crystals it stirred with a stirrer 114A, the slurry is subjected to slight ultrasonic vibration generated by the ultrasonic generator 114B. By doing so, the acid is prevented from being included in the aggregate of the terephthalic acid fine crystals, whereby, the pH value can be adjusted precisely and the terephthalic acid can be produced reliably.

The neutralization vessel 114 is usually smaller than the crystallization vessel 105, for example, the.neutralization vessel 114 is in the order of 1/50 to 1/500 the volume of the crystallization vessel 105. During the stirring with the stirrer 114A in the neutralization vessel 114, acid (sulfuric acid) is fed into a stirring shaft. For example, the stirrer 114A is configured so that an agitating blade 114C has a though hole 114D, which is communicated with the stirring shaft. In this case, the sulfuric acid is passed through the stirring shaft to the through hole 114D, from which it is injected into the solution of salt of terephthalic acid (the slurry of the terephthalic acid crystals). Thus, sting effect and mixing effect can be improved. Additionally, comparing with a case where the acid (sulfuric acid) is just introduced from the top of the neutralization vessel 114, such construction gives another effect. Precisely, the acid is prevented from being included in each terephthalic acid fine crystal. Therefore, the resulting terephthalic acid crystals have uniform particle sizes.

The slurry of the terephthalic acid crystals is collected in the crystallization vessel 105, where this slurry is stirred, so that the particle size of each terephthalic acid crystal can be grown uniformly.

Figure 5A:
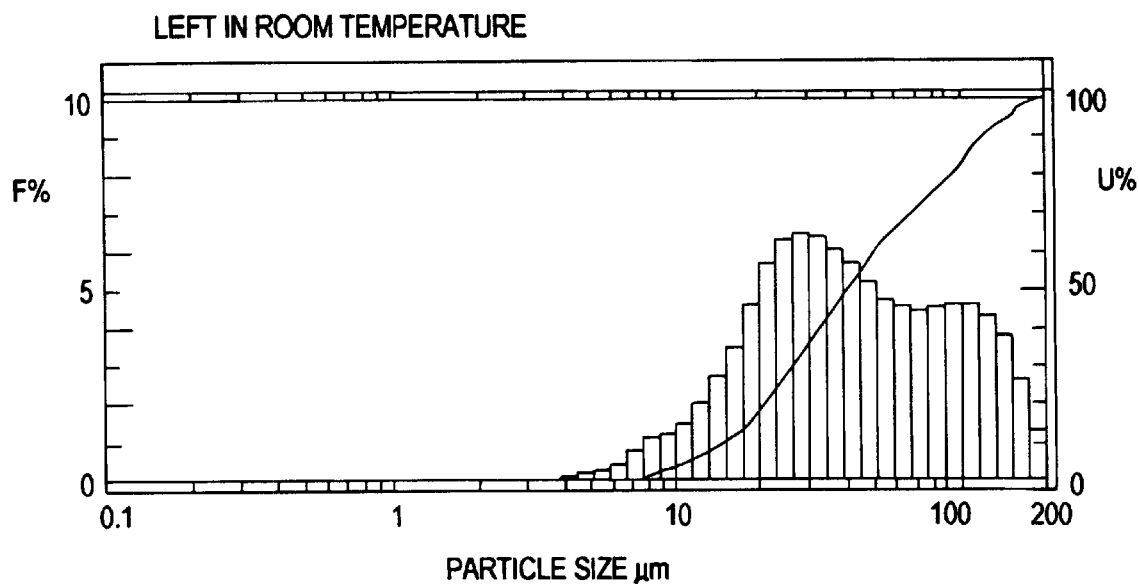
FIGS. 5(A) and 5(B) are graphs of particle size distribution of terephthalic acid when heating is carried out and not carried out in neutralization step, respectively.
Figure 5B:
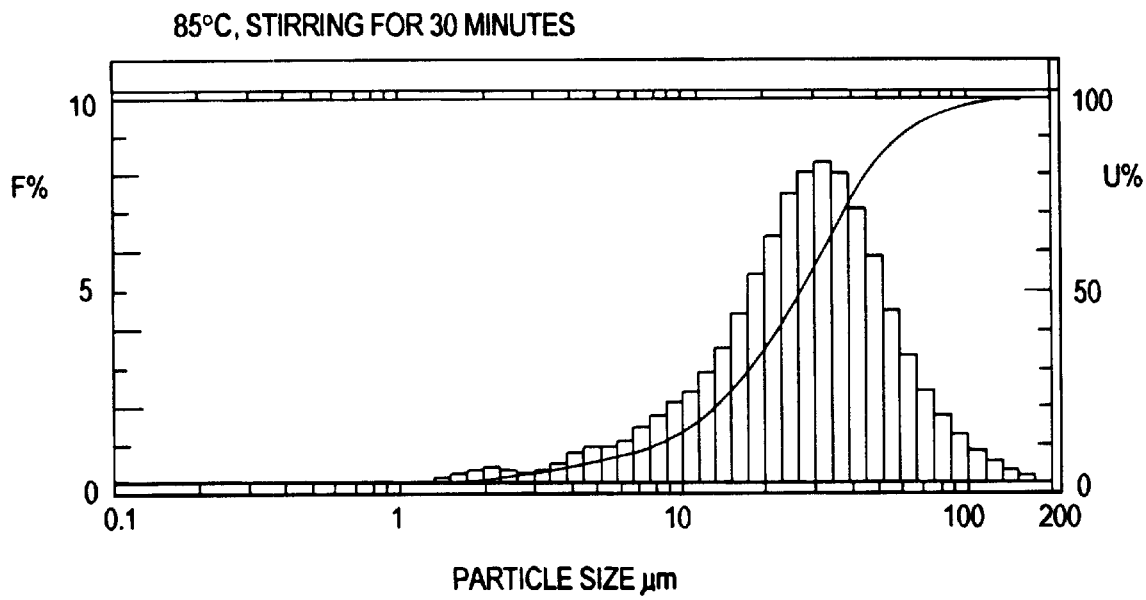

The stirring is, in the crystallization vessel 105, performed at the constant temperature of 50 to 95 ° C., e.g., about 85° C. and uniformly grown crystals are discharged from the bottom of the crystallization vessel 105 by means of a pump 45. Thus, the particle size distribution of terephthalic acid crystals is illustrated uniformly. See FIGS. 5(A) and 5(B), which show the distribution at the room temperature and at the increased temperature, respectively. Finally, in the next solid-liquid separation, filtration velocity can be increase, as shown in Table 1.

TABLE 1

| Temperature in the neutralization | Filtration velocity |
|---|---|
| 85° C. | 18.7 kg-DS/m$^2$.Hr |
| Room temperature | 5.7 kg-DS/m$^2$.Hr |

<Solid-Liquid Separation, Washing Step>

The resulting slurry of the terephthalic acid crystals obtained from the neutralization, crystallization step is passed through a transport pipe 17 to a solid-liquid separator, e.g., crossfeed belt type vacuum filter 106.

Figure 6:
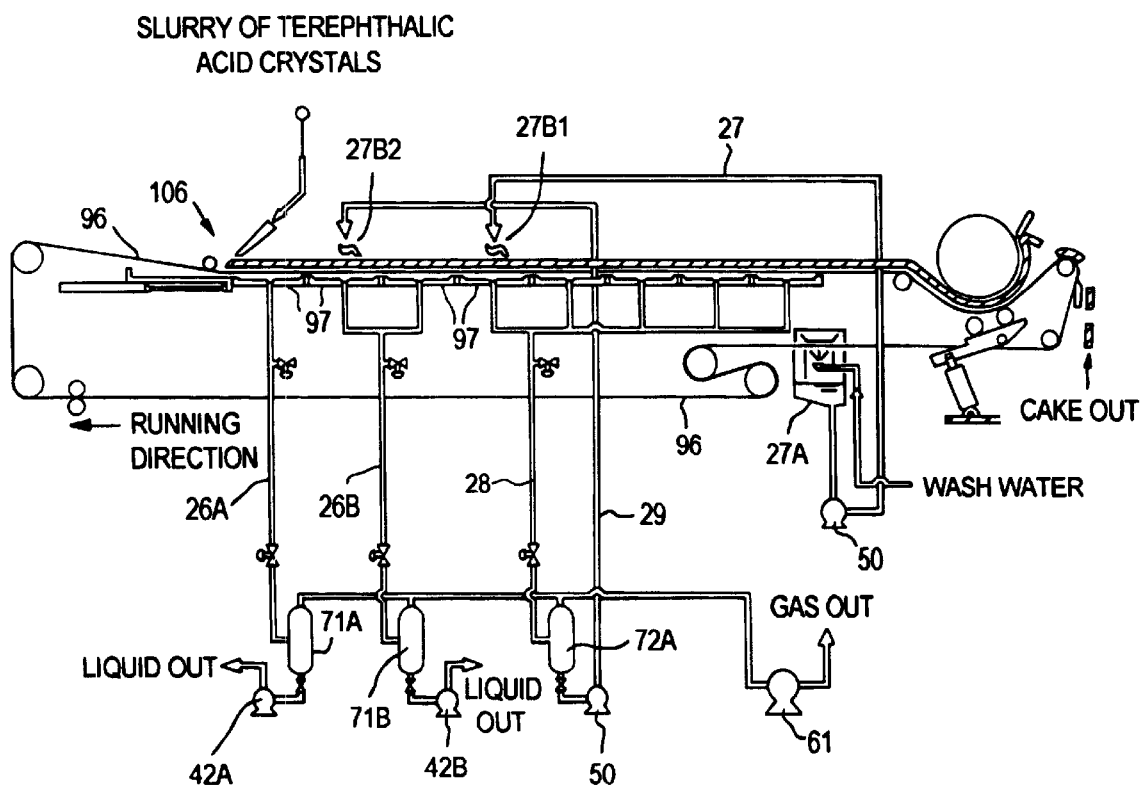
FIG. 6 is a schematic illustration of a crossfeed belt type vacuum filtering dissolver.

This crossfeed belt type vacuum filter 106 will now be described in detail below with reference to FIG. 6. First, the slurry is supplied to a running filter cloth 96, by which the slurry is fed along the horizontal direction (left side to right side in this figure). During this feeding, the acid and the alkali salt are filtered by vacuum suction, by means of a vacuum pump 61, at a vacuum box 97, which runs in the same way as the filter cloth 96. After this, they are passed through a transport pipe 26A to a filtrate separator 71A, and they are collected there.

The filter cloth 96 is washed with hot water. This wash water is passed to a filter cloth washer 27A, and the wash water is collected there temporally. Continuously, it is passed through a transport pipe 27 to a washer 27B1, and the wash water is collected there. This collected wash water is used for washing terephthalic acid. The terephthalic acid is obtained from the slurry, which is filtered by suction in order to remove alkali salt. After the washing of the terephthalic acid, the wash water is filtered by suction at the vacuum box 97 by means of the vacuum pump 61. Then, the wash water is passed through a transport pipe 28 to a filtrate tank 72A, and the wash water is collected there. The wash water collected in the filtrate tank 72A is discharged therefrom and passed through a transport pipe 29 to a washer 27B2, and it is collected and re-used for washing the terephthalic acid.

After this washing, the reused wash water is filtered by suction at the vacuum box 97 by means of the vacuum pump 61. Then, the wash water is passed through a transport pipe 26B to a filtrate separator 71B and the wash water is stored there. This stored wash water man be re-used for washing the terephthalic acid.

As shown in Table 2, such counter-flow type washing improves the purity of resulting terephthalic acid.

TABLE 2

| Cake wash ratio (1/kg-DS) | Purity of terephthalic acid (after dried) |
| --- | --- |
| 5 | 91.9% |
| 10 | 97.7% |
| 20 | 98.3% |

<Condensation, Crystallization, Separation of Mirabilite (recovering of alkali salt)>

The alkali salt collected from the filtrate separator 71A, 71B is passed through a transport pipe 20 to a filtrate tank 83, and the alkali salt is stored there temporally. Then, the alkali salt is discharged therefrom and passed through a transport pipe 21 and through a heater 32 for the evaporation of water to a crystallizer 33.

In the crystallizer 33, the pressure is reduced by means of a vacuum pump 62. Accordingly, the water included in slurry of the alkali salt is vaporized, the resulting steam is condensed by cooling so as to be re-used as the water for the solid-liquid separation, dissolution, impurities-removing step or as the wash water for the filter cloth and cake in solid-liquid separation, washing step.

Slurry of crystals is discharged from the crystallizer 33 and passed through a transport pipe 19 to a centrifugal separator 108. In this centrifugal separator 108, the slurry is subjected to solid-liquid separation so that alkali salt, ethylene glycol and alkali can be obtained. The separated alkali salt is passed to an indirect beating dryer, e.g., puddle type rotary vacuum drier 109 con g de so as to be provided with a jacket 94 and a shaft 95, through both of which heat medium can be recycled, by means of a belt conveyor 113. In the drier 109, the alkali salt is dried in a vacuum, and the alkali salt having high purity can be recovered there.

When sulfuric acid is used in the neutralization step, mirabilite c be obtained as the alkali salt, which can be used as a product having many kinds of usage.

On the other hand, the separated ethylene glycol and alkali are discharged from the centrifugal separator 108 and passed through a transport line 23 to the filtrate tank 84, and the separated ethylene glycol and alkali are stored there temporally. Then, the ethylene glycol and the alkali are discharged from the filtrate tank and passed through a transport line 24 to the above mentioned filtrate tank 81, and the ethylene glycol and the alkali are mixed. After this, operation is continued as mentioned above.

<Drying, Pulverization Step>

On the other hand, the terephthalic acid, which is washed in the crossfeed belt type vacuum filter 106, is passed to an indirect heating dryer, e.g., puddle type rotary vacuum drier 107 configured so as to be provided with a jacket 94 and a shaft 95, through both of which heat medium can be recycled, by means of a belt conveyor 112. In the drier 107, the pressure is reduced by means of a vacuum pump 63. Accordingly, the terephthalic acid can be dried in a vacuum quickly and without deterioration, whereby the terephthalic acid having high purity can be recovered. Steam generated by the drying is passed through a transport pipe 25 and condensed by cooling. Thus, the resulting water is passed through a transport pipe 22 to the filtrate tank 83, and the water is collected there.

After that, pulverization of recovered terephthalic acid can be carried out by a known method.

Figure 7:
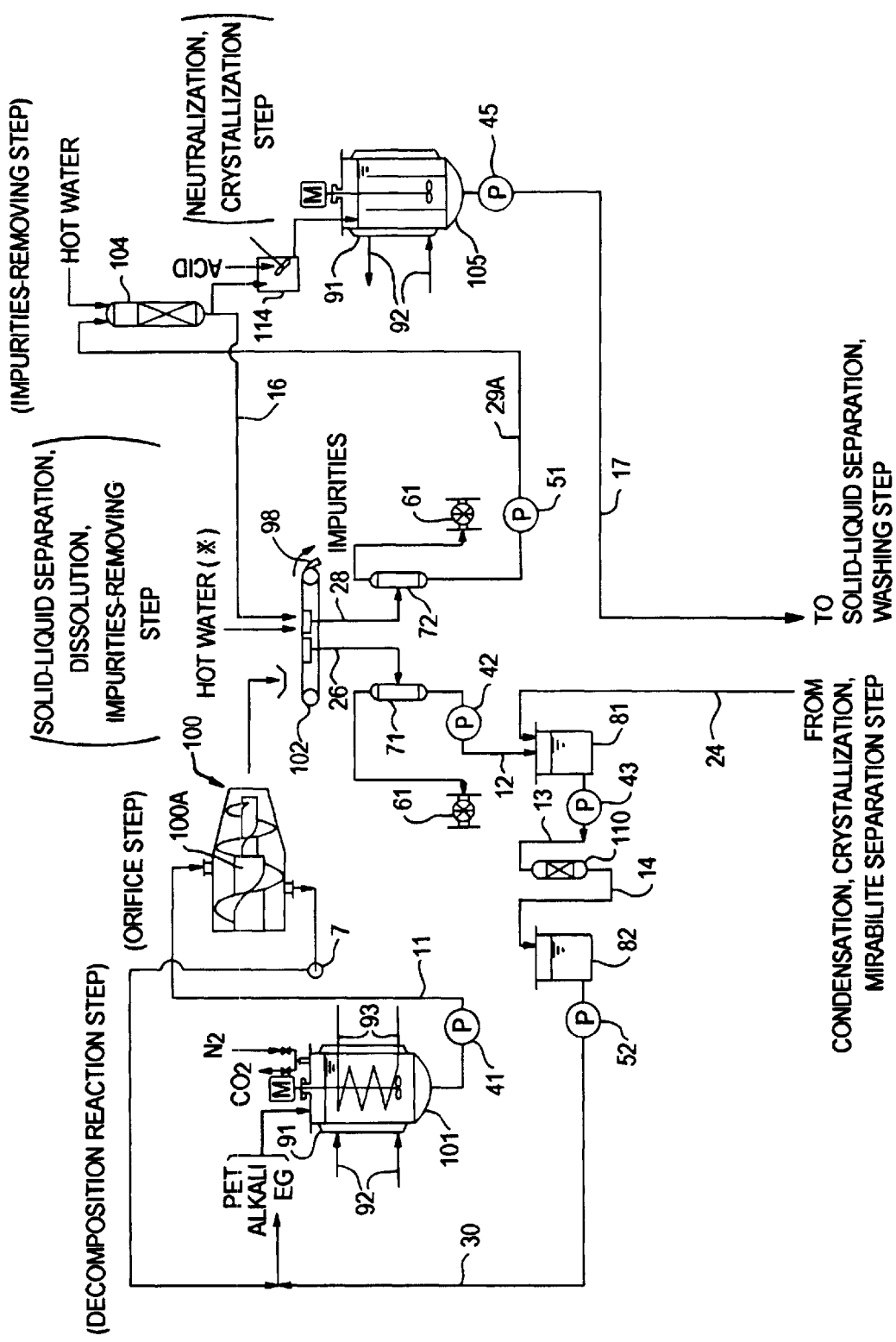
FIG. 7 is a flow diadem of the whole second embodiment in accordance with the first aspect of the present invention.

The Second Embodiment in Accordance with the First Aspect of the Present Invention FIG. 7 shows the second embodiment in accordance with the first aspect of the present invention. In this embodiment, in decomposition reaction step, decomposition reaction is carried out in a vertical type cylindrical stirrer 101. The vertical type cylindrical stirrer 101 is equipped with a heating jacket 91 on its external periphery, through which heat medium 92 is passed, and this stirrer 101 includes a cooling coil 93 for adjusting temperature. Stirring operation is carried out in the stirrer 101, for example, for 30 to 90 minutes at the temperature of 120 to 190° C. under the atmospheric pressure, whereby the decomposition reaction can be attained.

Deposition reaction slurry of salt of terephthalic acid and ethylene glycol is discharged from the stirrer 101 and passed, by means of a pump 41, through a transport pipe 11 to a crossfeed belt type vacuum filtering dissolver 102 directly or after orifice operation at an orifice 100.

The orifice 100 is configured so as to have structure of screw press type and so as to have a screw conveyor 100A, which is tapered and placed therein. Ethylene glycol can be returned from the suitable point of the body portion of the orifice 100 to the vertical type cylindrical stirrer 101 by means of a pump 7. Provision of the orifice 100 decreases the amount of required ethylene glycol. Additionally, filtration efficiency of the next filtration stop (solid-liquid separation) per hour can be improved.

The Embodiment in Accordance with the Second Aspect of the Present Invention

Figure 8:
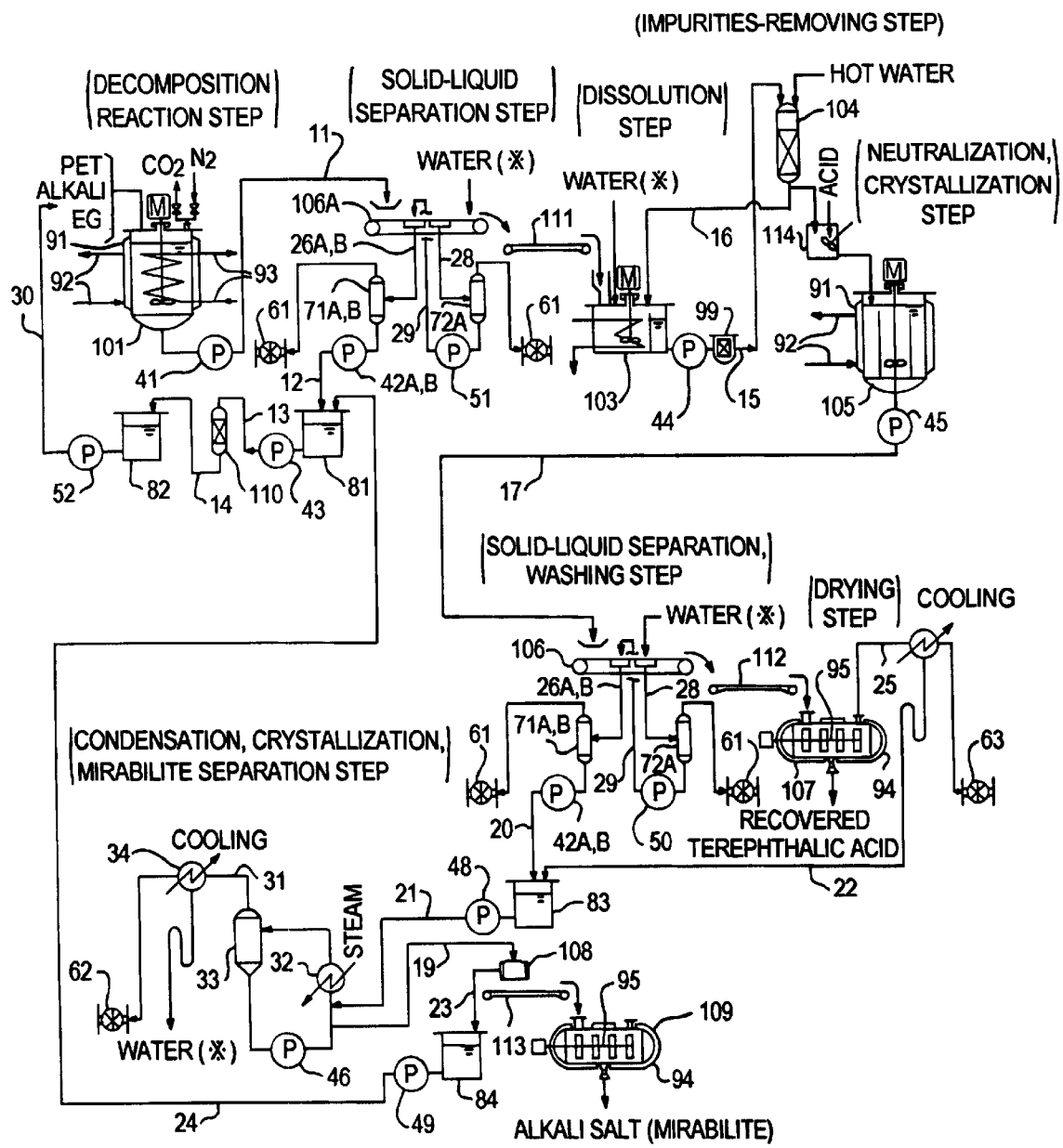
FIG. 8 is a flow diagram of the whole embodiment in accordance with the second aspect of the present invention.
Figure 9:
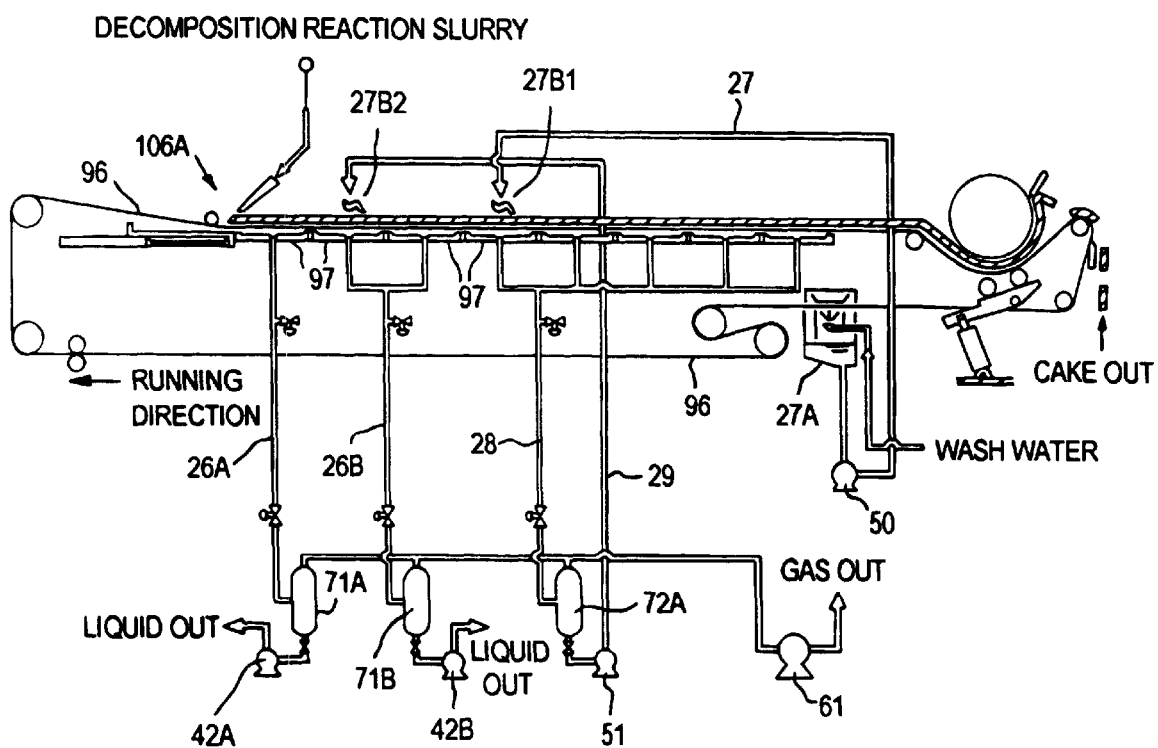
FIG. 9 is a schematic illustration of a crossfeed belt type vacuum filtering dissolver, which is used for solid-liquid separation in a proceeding stage in the whole embodiment in accordance with the second aspect of the present invention.

FIGS. 8 and 9 show the embodiment in accordance with the second aspect of the present invention. In this embodiment, in the same way as the second embodiment in accordance with the first aspect of the present invention, decomposition reaction is carried out in a vertical type cylindrical stirrer 101.

Decomposition reaction slurry obtained from the decomposition reaction in the vertical type cylindrical stirrer 101 is discharged therefrom and passed to a crossfeed belt type vacuum filter 106A, which is configured in the same; way as the crossfeed belt type vacuum filter 106 in the later stage in the first embodiment. Then, at the crossfeed belt type vacuum filter 106A, ethylene glycol is removed from the slurry and washing is performed with a wash liquid (water).

After the ethylene glycol is removed, the salt of terephthalic acid can be recovered and is charged into a vertical type cylindrical stirrer 103, which is provided separately from the crossfeed belt type vacuum filter 106A, by means of a cake transport belt conveyor. Hot water is charged into the vertical type cylindrical stirrer 103 at about 80° C. In this case, the hot water is used 3 times as much as the salt of terephthalic acid. Can be used, as the hot water, the above mentioned regenerated water in this system as well as regenerated wash water, which is discharged from a vertical type adsorptive active carbon packed cylindrical column 104 and passed through a transport pipe 16.

The solution of salt of terephthalic acid is passed through a transport pipe 15 to a soluble impurities-removing step e.g., the vertical type adsorptive active carbon packed cylindrical column 104 by means of a pump 44. It is preferable that before this removing operation, insoluble impurities are removed with a check filter 99 equipped to the vertical cylindrical stirrer 103 or the like so that the solution of salt of terephthalic acid is fed to the impurities-removing step while the insoluble impurities are not finally contained in the solution.

In this embodiment, similar to the second embodiment in accordance with the first aspect of the present invention, decomposition slurry of the salt of terephthalic acid and ethylene glycol can be subjected to orifice operation at an orifice (100 in FIG. 7) before being fed into a crossfeed belt type vacuum filter 106A.

Other Embodiments

As stated before, in order to separate the ethylene glycol from the decomposition reaction slurry of salt of terephthalic acid and the ethylene glycol, instead of the crossfeed belt type vacuum filtering dissolver 102, other separators such as centrifugal separator can be used. Further, it is possible that the elements of the above embodiments are suitably combined so as to form systems according to the present invention.

BASIC EXAMPLE

A vertical type cylindrical stirrer, which has the size of 150 mm diameter by 200 mm height and which is equipped with a beating jacket on its external periphery, is filled with ethylene glycol. After the ingredients are heated to the temperature of 170° C., 600 g of pulverized products of spent PET, each having the shape of 6 to 8 mm square, and 330 g of sodium carbonate are charged into the stirrer. Then, the ingredients are reacted for 40 minutes while they are stirred. Next, the ethylene glycol and sodium terephthalate are separated from the resulting reaction slurry by centrifugal separation. Then, the separated ethylene glycol and sodium terephthalate are dried for 2 hours in a vacuum oven at the temperature of 130° C. for sufficient dehydrating. Therefore, dried solid (sodium terephthalate, insoluble PET and solid impurities) and filtrate (ethylene glycol and insoluble impurities) are obtained. From the filtrate, the insoluble impurities are separated by distillation and ethylene glycol is recovered for re-using.

On the other hand, the dried solid is dissolved into water. The water is used 5 times as much as the dried solid Then, from the solution, insoluble solid impurities are removed by centrifugal separation. Next, the resulting filtrate is fed into a multi-stage active carbon packed column (, in which particle size of each active carbon is sequentially decreased downwardly and a cation exchange resin bed is provided at a middle stage). In this column, soluble impurities are removed from the filtrate, hence 7000 cc of solution of sodium terephthalate having high purity can be obtained.

Into the solution of sodium terephthalate, about 310 g of concentrated sulfuric acid is added for neutralization, while the solution is stirred until the pH value of the solution is adjusted to be about 2. Then, the neutralized solution is separated into terephthalic acid cake and solution of sodium sulfate by centrifugal separation. The terephthalic acid cake is washed with water sufficiently and dried so that 510 g of terephthalic acid is recovered. Its purity was 99.9% and recovery was 98.5%. On the other hand, the solution of sodium sulfate is heated for dehydrating so that mirabilite can be recovered.

Example 1

Corresponding to the First Embodiment in Accordance with the First Aspect of the Present Invention A heating reactor used for this example has the size of 200 mm diameter and 1000 mm length. The reactor has a feed section, decomposition reaction section, extruding section, and orifice tapered section. The orifice tapered section is 200 mm long and its diameter is decreased toward its tip end from 200 mm to 100 mm. This reactor has also a screw with a vane, which is placed longitudinally in the reactor. The vane's pitch is 10 mm at the feed section and 5 mm at the decomposition reaction section, extruding section, and the orifice tapered section. First, the heating reactor is filled with ethylene glycol and heated to the temperature of 170° C. Then, about 5 kg of pulverized spent PET (flakes each having the shape of 5 to 8 mm square) and 2.7 kg of sodium hydrate are continuously charged into the heating reactor at the rate of 80 g/min and 40 g/min, respectively. Then, decomposition reaction is continuously carried out in the reactor for 1 hour at the screw rotary speed of 5 rpm.

Next, exuded and discharged slurry of sodium terephthalic containing 30% of ethylene glycol is fed to a crossfeed belt type vacuum filtering dissolver and the slurry is laid on the dissolver with its thickness of about 6 mm. The crossfeed belt type vacuum filtering dissolver has the size of 300 mm wide and 5000 mm long (4000 mm for filtration by suction and 1000 mm for dissolution). Then, the slurry is filtered by suction at the suction speed of 3.5 cm/min, hence the thickness of the slurry is decreased to about 4 mm. This slurry is dissolved into water having the amount of 5 times as much as the slurry. Next, the resulting solution of sodium terephthalate is introduced into an active carbon column having the size of 200 mm diameter by 500 mm length. In this active carbon column, soluble impurities are removed at the flow rate of 250 cc/min. Continuously, the solution is introduced into a neutralization chamber together with the 70 cc/min of sulfuric acid having the pH value of 4. In the neutralization chamber, the solution and the sulfuric acid are stirred while ultrasonic vibration is applied. The crystallized terephthalic acid and water are discharged from the bottom of the neutralization chamber and supplied to a crossfeed belt type vacuum filter. In this filter, the terephthalic acid is washed in counter-flow washing and dried and pulverized in a puddle type rotary vacuum drier equipped with a crusher. Finally, 3.2 kg of terephthalic acid having the high purity and exhibiting the sharp particle size distribution can be obtained. Its purity is 99%, particle size distribution is 35 $\mu$+/−20 $\mu$, and recovery is 95.4%.

The solution of sodium sulfate collected in the filter gives crystal mirabilite by means of a condensation, crystallization, mirabilite-separation step. Additionally, the water generated from steam is used for the counter-flow wash.

Example 2

Corresponding to the Embodiment in Accordance with the Second Aspect of the Present Invention Shown in FIG. 8

In the embodiment in accordance with the second aspect of the present invention shown in FIG. 8, finally obtained terephthalic acid has similar purity, particle size distribution and recovery to those of Example 1.

The First Embodiment in Accordance with the Third Aspect of the Present Invention The pulverized products of spent PET are formed by crushing PET bottles or the like. Then, each PET article has many parts made of different materials, thus time required for decomposition reaction is different for each part. In this connection, one example will be stated below. First, 150 g of pulverized products of PET is supplied to 500 g of EG and this reactor is heated to the temperature of about 180° C. Then, 90 g of sodium carbonate is added and stirring is performed for 25 minutes at the rotary speed of 300 rpm. In this stirring operation, some pulverized products of spent PET are not decomposed depending on the material of each part, as shown in Table 3.

TABLE 3

| Sample | | Amount of remained products (g) | Amount of remained products (%) |
|---|---|---|---|
| Crystal nozzle part | Whitened part | 28 | 19.0 |
| Drawing body part | Transparent part | 2 | 1.3 |
| Amorphous part | Un-crystallized part | 64 | 43.0 |

Accordingly, in order to decompose completely the pulverized products of spent PET derived from many parts, it takes time long enough to decompose a part where the decomposition reaction is slowest among all the parts. Precisely, in a certain part where the decomposition reaction is fast, even after the completion of decomposition reaction of this part, the reaction is continued due to the part where the decomposition reaction is slowest, resulting in low efficiency.

In this connection, in the third aspect of the present invention, since the decomposition reaction step is constructed from equal to or more than two stages, i.e., multiple stages, the decomposition reactions in the parts of the pulverized products are performed in corresponding stages, respectively, so that the reactions in these all parts can be finished simultaneously, resulting in high efficiency.

Figure 10:
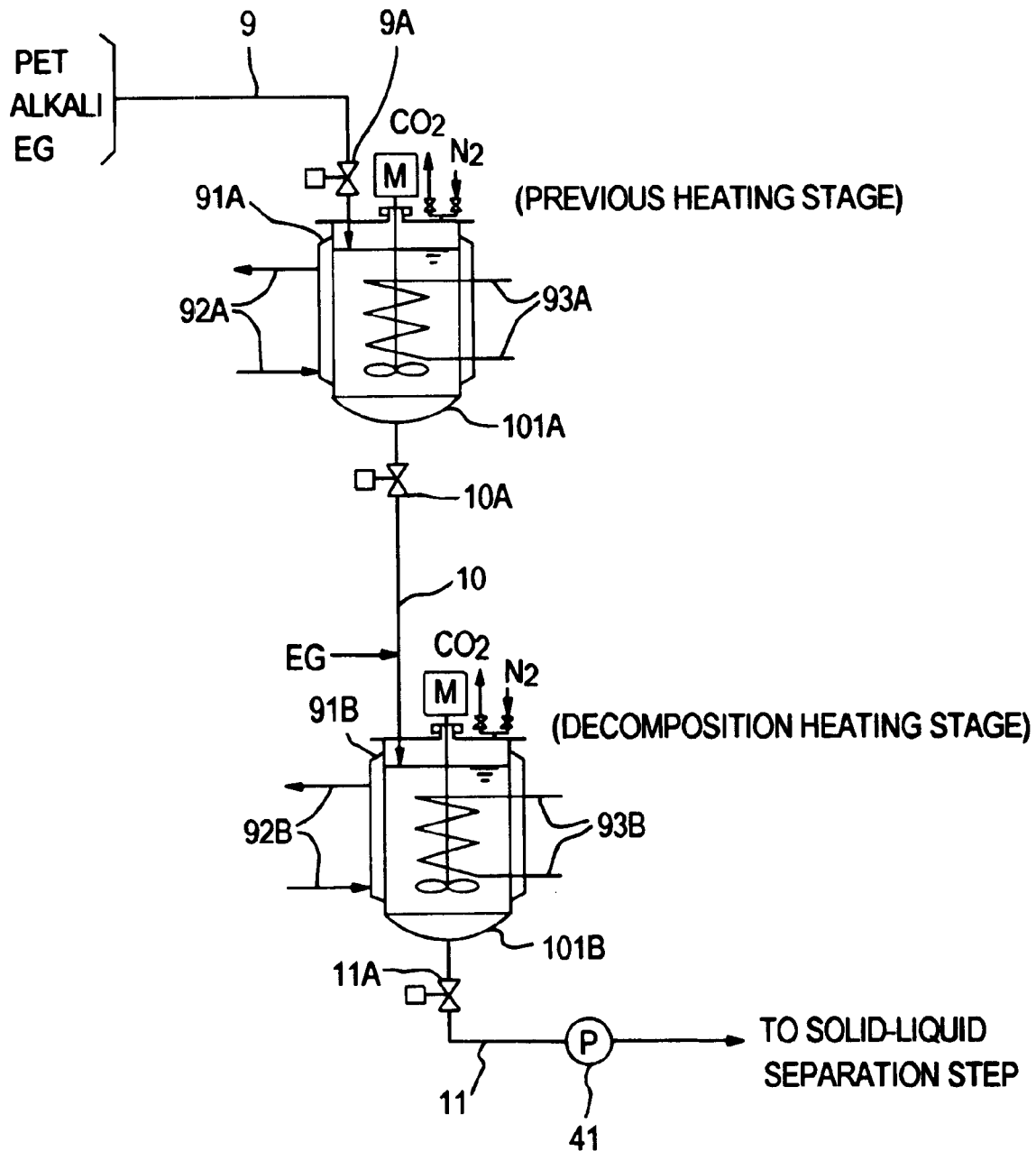
FIG. 10 is a flow diagram of the whole first embodiment in accordance with the third aspect of the present invention.

FIG. 10 shows the first embodiment in accordance with the third aspect of the present invention. In this embodiment, decomposition reaction is carried out in the two stages. In the first stage, previous heating is performed in a vertical type cylindrical stirrer 101A at the temperate range from 100° C. to the temperature at which the decomposition reaction for the pulverized products of spent PET is not substantially stated, for 5 minutes or more, preferably 20 minutes or more. Then, in the second stage, decomposition reaction heating is performed in a vertical type cylindrical stirrer 101B at the temperature range from the temperature at which the decomposition reaction for the pulverized products of spent PET is substantially started to the boiling point of solvent.

Particularly, in this embodiment, since EG is used as the solvent, it is preferable that the previous heating stage is performed at the temperature of 100 to 140° C. and the decomposition reaction heating stage is performed at the temperature of 130 to 180° C. The higher moisture contained in the solvent, the lower temperature at which the decomposition reaction for the pulverized products of spent PET is started. In this connection, according to this embodiment, since EG is used as the solvent instead of water, the decomposition reaction is started at 130 to 140° C. In the decomposition reaction, vaporization of solvent would increase the amount of required solvent and the boiling point of EG is 196° C. Therefore, the decomposition reaction heating stage is performed at the temperature of 180° C. or lower.

The vertical type cylindrical stirrer 101A, 101B can be configured in the same way as the vertical type cylindrical stirrer 101, which is used in the decomposition reaction step in the above mentioned embodiment. Precisely, the vertical type cylindrical stirrer 101A, 101B are equipped with heating jacket 91A, 91B on the external periphery thereof, through which heat medium 92A, 92B are passed, respectively. Then, this stirrer 101A, 101B include cooling coil 93A, 93B for adjusting temperature. Stirring operation is carried out at the suitable temperature corresponding to each stage under the atmospheric pressure.

First, PET, alkali and EG are passed through a transport pipe 9 to the vertical type cylindrical stirrer 101A with flow control by a valve 9A. In this embodiment, the mass ratio of pulverized products of spent PET to EG is determined so as to be 1:0.8 to 1.2. In the vertical type cylindrical stirrer 101A, PET, alkali and EG are previously heated and stirred. The resulting slurry is passed through a transport pipe 10, to the vertical type cylindrical stir 101B with flow control by a valve 10A. In this embodiment, in the vertical type cylindrical stirrer 1013, if desired, EG is added again until the mass ratio of pulverized products of spent PET to EG is 1:2.0 to 2.5. Then, the ingredient is subjected to the decomposition reaction and stirred so that the salt of terephthalic acid and EG are obtained. The decomposition reaction slurry is passed, by means of a pump 41, through a transport pipe 11 to a solid-liquid separation step with flow control by a valve 11 After this, operation is continued in the same way as the treatment stated referring to FIG. 1.

Figure 11:
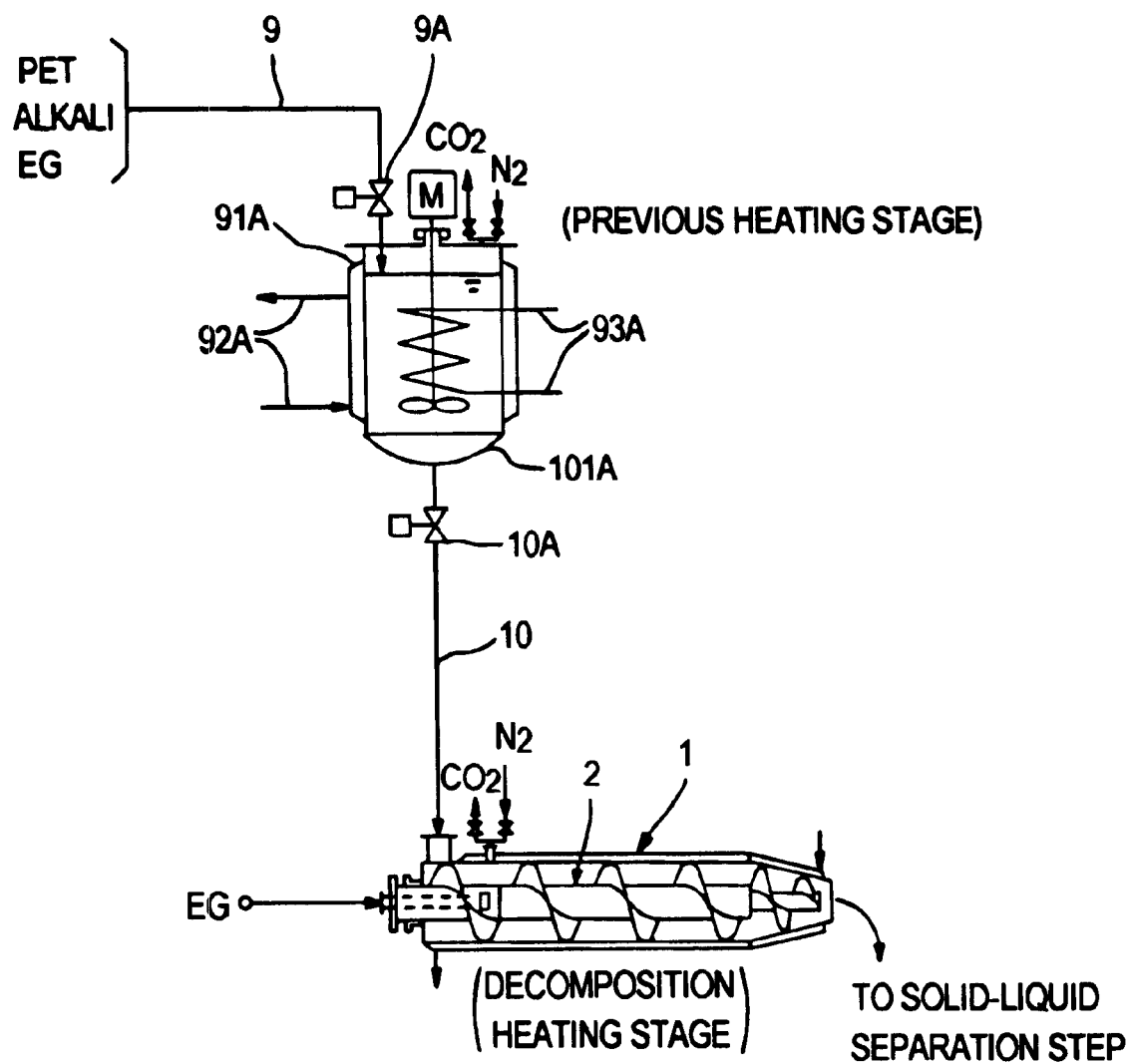
FIG. 11 is a flow diagram of the whole second embodiment in accordance with the third aspect of the present invention.

The Second Embodiment in Accordance with the Third Aspect of the Present Invention FIG. 11 shows the second embodiment in accordance with the third aspect of the present invention. FIG. 11 shows two steps corresponding to the previous heating step and decomposition reaction step shown in FIG. 10, respectively. In this embodiment, instead of the vertical type cylindrical stirrer 101B of the first embodiment in accordance with the third aspect of the present invention, a screw press type horizontal decomposition reactor is used. This decomposition reactor is configured in the same way as the reactor shown in FIG. 1. Slurry, which is obtained by previously beating PET, alkali and EG and stirring them, is charged through a transport 10 to a charge inlet 3 of the screw press type horizontal decomposition reactor 1 with flow control by a valve 10A. If desired, EG is charged into a charge inlet 4. Then, mainly in body portion, the pulverized products of spent PET are subjected to decomposition reaction so that salt of terephthalic acid and EG are continuously obtained. The decomposition reaction slurry is exuded from a tapered portion 1B and passed to a solid-liquid separation step. After this, operation is continued in the same way as the treatment stated referring to FIG. 1.

Figure 12:
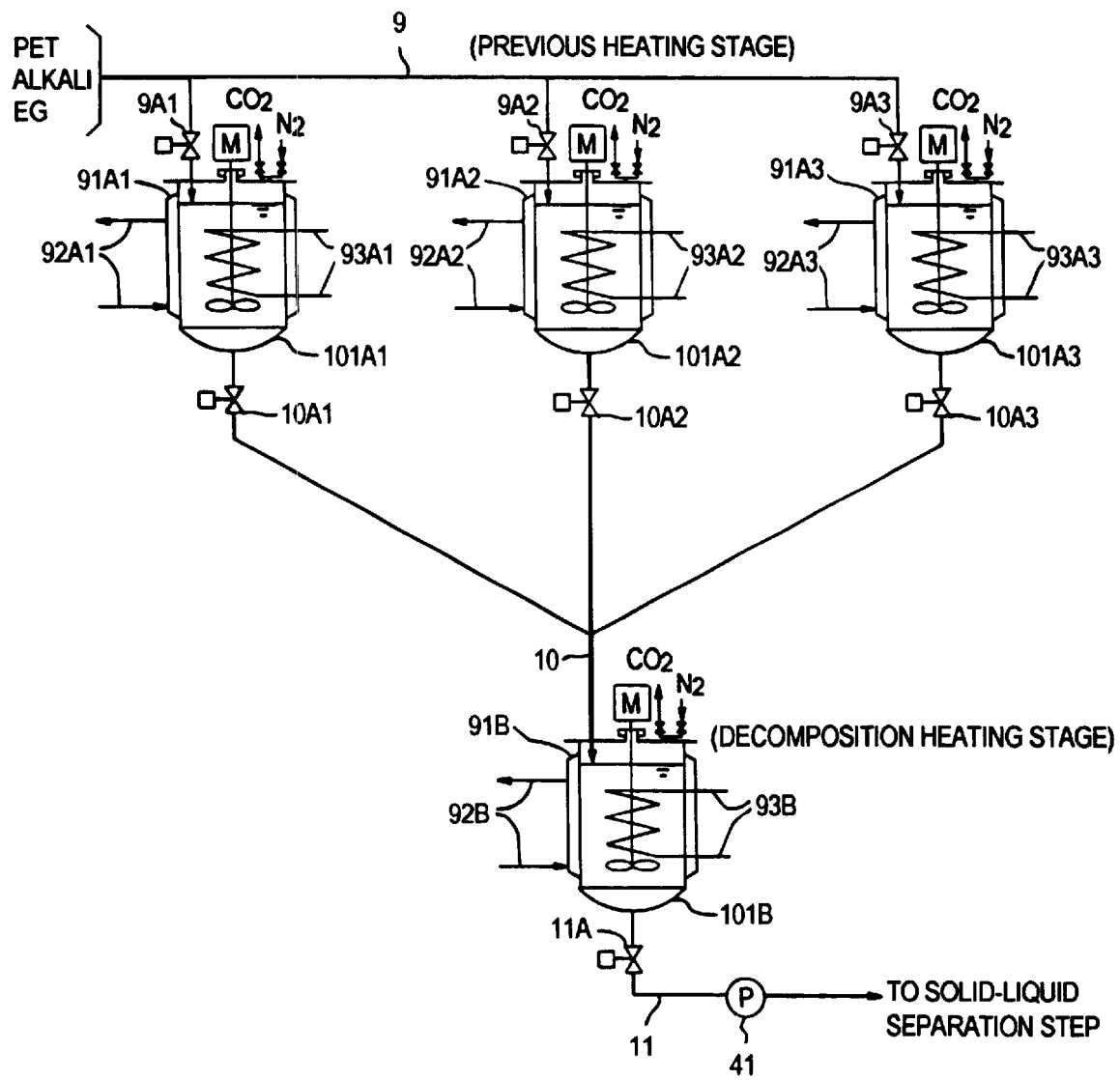
FIG. 12 is a flow diagram of the whole third embodiment in accordance with the third aspect of the present invention.

The Third Embodiment in Accordance with the Third Aspect of the Present Invention FIG. 12 shows the third embodiment in accordance with the third aspect of the present invention. In this embodiment, instead of the vertical type cylindrical stirrer 101A of the first embodiment in accordance with the third aspect of the present invention, three vertical type cylindrical stirrers 101A1, 101A2 and 101A3 are used for the previous heating performed in parallel operation. This decomposition reactor is configured in the same way as the reactor shown in FIG. 1. Generally, time required for the previous heating where the pulverized products of spent PET are crystallized is longer than time required for the decomposition reaction where the pulverized products of spent PET are subjected to the decomposition reaction. Therefore, like the parallel operation in this embodiment, if the previous heating is carried out with a plurality of vertical type cylindrical stirrers, the decomposition reaction can be carried out continuously with vertical type cylindrical stirrer 101B.

First, PET, alkali and EG are passed through a transport pipe 9 to the vertical type cylindrical stirrers 101A1, 101A2 and 101A3 with flow control by valves 10A1, 10A2 and 10A3. In the vertical type cylindrical stirrers 101A1, 101A2 and 101A3, PET, alkali and EG are previously heated and stirred. The resulting slurry is passed through a transport pipe 10, to the vertical type cylindrical stirrer 101B with flow control by valves 10A1, 10A2 and 10A3. After this, operation is continued in the same way as the treatment stated referring to FIG. 1.

Impurities such as polypropylene (PP) and polyethylene (PE) are often contained in the pulverized products of spent polyethylene terephthalate. These impurities float on the solvent such as ethylene glycol (EG) because of smaller specific gravity than that of the solvent, as shown in Table 4. However, in the embodiments stated above, these impurities are not removed before heating.

TABLE 4

| Substance | Specific gravity |
|---|---|
| PP | 0.90 |
| PE | 0.91 to 0.97 |
| EG | 1.1155 |
| PET | 1.56 to 1.69 |

Accordingly, before the heating stage, there can be provided a stage where the impurities, which float on the solvent because of the smaller specific gravity than that of the solvent, are removed.

Example 3

A vertical type cylindrical stirrer, which has the size of 150 mm diameter by 200 mm height and which is equipped with a heating jacket on its external periphery, is filled with 1200 g of EG. After the ingredients are heated to the temperature of 150° C., 600 g of pulverized products of spent PET, each having the shape of 6 to 8 mm square, and 360 g of sodium carbonate are charged into the stirrer. Then, the ingredients are stirred for 10 minutes (the previous heating step).

Next, the resulting slurry is fed into a vertical type cylindrical stirrer configured in the same way as the vertical type cylindrical stirrer of the previous heating step. 600 g of EG is added again. Then, the ingredients are heated to the temperature of 180° C. and stirred for 10 minutes (decomposition reaction).

From the decomposition reaction slurry, solid salt of terephthalic acid is separated. The reminder is dissolved into water. Finally, all amount of PET is reacted, i.e., 100% of PET can be used in the decomposition reaction.

Comparative Example 1

A vertical type cylindrical stirrer, which has the size of 150 mm diameter by 200 mm height and which is equipped with a heating jacket on its external periphery, is filled with 1800 g of EG. After the ingredients are heated to the temperature of 180° C., 600 g of pulverized products of spent PET, each having the shape of 6 to 8 mm square, and 360 g of sodium carbonate are charged into the stirrer. Then, the ingredients are stirred for 30 minutes.

From the decomposition reaction slurry, solid salt of terephthalic acid is separated. The rreminder is dissolved into water. Finally, 22 g of PET is not reacted, i.e., 96.3% of PET can be used in the decomposition reaction.

Therefore, by the provision of the previous heating step, recovery of terephthalic acid can be increased, further, reaction can be progressed quickly.

The Embodiment in Accordance with the Fourth Aspect of the Present Invention

Figure 13:
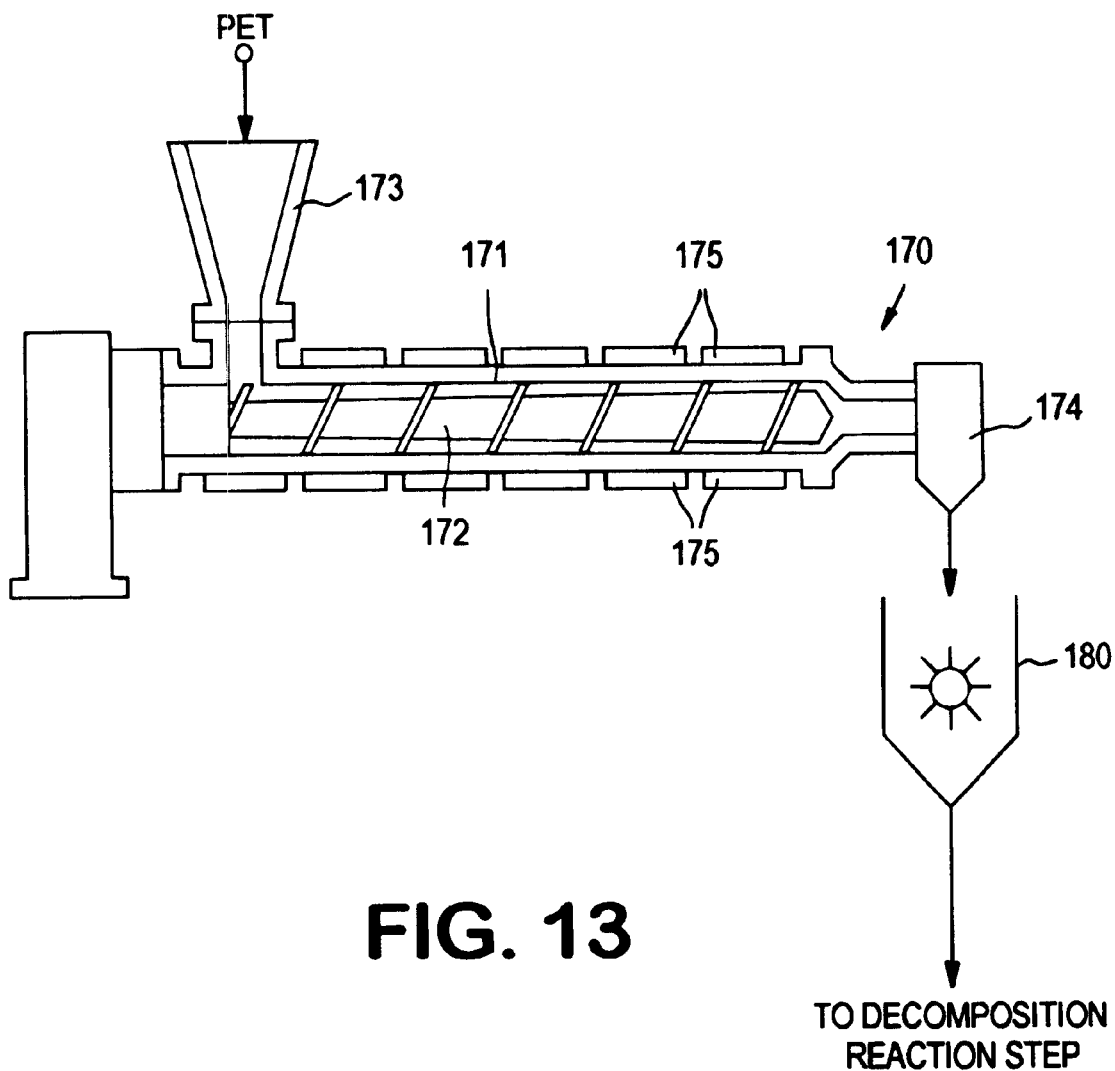
FIG. 13 is a simplified cross sectional view of a screw extruder used for the fourth aspect of the present invention.

In the fourth aspect of the present invention, previous to the above decomposition reaction (thermal cracking) step, the pulverized products of spent PET are subjected to thermal degradation. The thermal degradation operation can be carried out with a thermal degradation apparatus, e.g., screw extruder 170 shown in FIG. 13. The screw extruder 170 comprises an external cylinder 171, inside of which is kept at a vacuum; and a screw 172, which is placed longitudinally in and co-axially with the external cylinder 171. Then, a hopper 173 is mounted on the upper side of the external cylinder 171 and the pulverized product of spent PET are charged from the hopper 173. On the other hand, a die 174 is connected to the, tip end of the external cylinder 171 and the thermal degraded pulverized products of spent PET are discharged form the die 174. Further, a heating jacket 175 is provided on the external periphery of tie screw extruder 170 and heat medium is passed through this jacket 175.

First, the pulverized products of spent PET are charged through a hopper 173 to the screw extruder 170. Then, the pulverized products of spent PET are fed toward the fore end of the extruder (from the left side to the right side in this figure) with the screw 172 placed in the external cylinder 171. Thus, the pulverized products of spent PET are heated by the jacket 175 and subjected continuously to the thermal degradation.

This heating is preferably performed at the temperature of 290 to 330° C. for 5 to 20 minutes.

Figure 14:
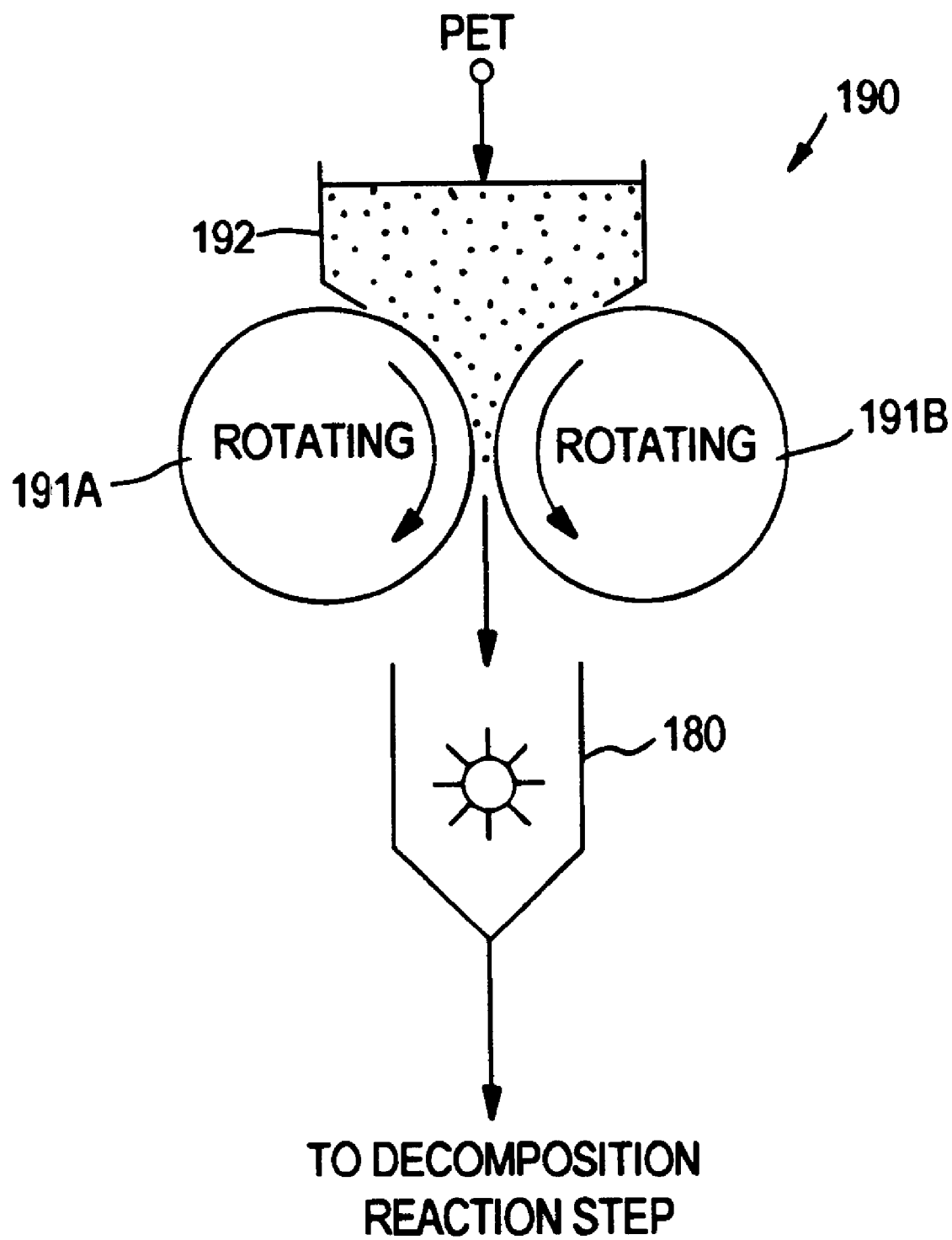
FIG. 14 is a simplified conceptual illustration of a heating roller used for the fourth aspect of the present invention.

Alternatively, the thermal degradation can be carried out by a heating roller 190, conceptually shown in FIG. 14. The beating roller 190 includes a PET charging equipment 192 and heating rolls 191A, 191B having axes different each other. The heating rolls 191A, 191B are heated to a suitable temperature, for example in this embodiment, 350° C. and rotated the direction by which the opposed surfaces of rolls are moved downward.

In order to discharge the pulverized products of spent PET, the pulverized products are fed downward through a gap formed between the heating rolls 191A and 191B. While the pulverized products are fed downward, they are heated and subjected continuously to the thermal degradation.

Thus resulting thermal degraded pulverized products of spent PET are, by a crusher 180, crushed into pieces each having the size in the order of 3 to 5 mm. Then, these pieces are fed to the next decomposition reaction step. After this, operation is continued in the same way as the treatment stated in the above embodiments except the following.

Precisely, in this embodiment, heat is to be used again in the next decomposition reaction step. Accordingly, it is preferable that the pulverized products of spent PET are continuously fed to the decomposition reaction step without brake for the effective use of heat obtained from the pulverized products of spent PET. As the decomposition reactor, other than the reactor stated in the basic embodiment, a reactor, which is configured in the same way as the above mentioned screw extruder 170, can be used. In this case, the pulverized products of spent PET, which have been subjected to the thermal degradation, as well as EG and alkali are charged through the hopper 173 to the screw extruder. Thus, the resulting slurry can be discharged through the die 174 from the extruder.

Example 4

The pulverized products of spent PET each of which has the shape of 6 to 8 mm square are fed continuously to a screw elder shown in the example in accordance with the fourth aspect of the present invention. Then, the pulverized products of spent PET is heated to the temperature of 280 to 300° C. so that the pulverized products of spent PET are subjected to thermal degradation. Next, the thermal degraded pulverized products of spent PET are further crushed into pieces each having the shape of 3 to 5 mm square (thermal degradation, crushing step).

A vertical type cylindrical stirrer, which has the size of 150 mm diameter by 200 mm height and which is equipped with a heating jacket on its external periphery is previously filled with 1800 g of EG and it is heated to the temperature of 180° C. Next, 600 g of the pulverized products of spent PET, which are subjected to the above thermal degradation, crushing step, and 360 g of sodium carbonate are charged into the vertical type cylindrical stirrer. Then, the ingredients are stirred for 15 minutes (decomposition reaction step).

The resulting decomposition reaction slurry was subjected to solid-liquid separation so that solid salt of terephthalic acid is obtained. Then, the solid salt is dissolved into water. Finally, all amount of PET is reacted, i.e., 100% of PET can be used in the decomposition reaction.

Comparative Example 2

A vertical type cylindrical stirrer, which has the size of 150 mm diameter by 200 mm height and which is equipped with a heating jacket on its external periphery is filled with 1800 g of EG and it is heated to the temperature of 180° C. Next, 600 g of the pulverized products of spent PET and 360 g of sodium carbonate are charged into the vertical type cylindrical stirrer. Then, the ingredients are stirred for 30 minutes (decomposition reaction step).

The resulting decomposition reaction slurry is subjected to solid-liquid separation so that solid salt of terephthalic acid is obtained. Then, the solid salt is dissolved into water. Finally, 22 g of PET is not reacted, i.e., 96.3% of PET can be used in the decomposition reaction.

Therefore, by the provision of the thermal degradation step before decomposition reaction step, recovery of terephthalic add can be increased, further, reaction can be progressed quickly.

Figure 15:
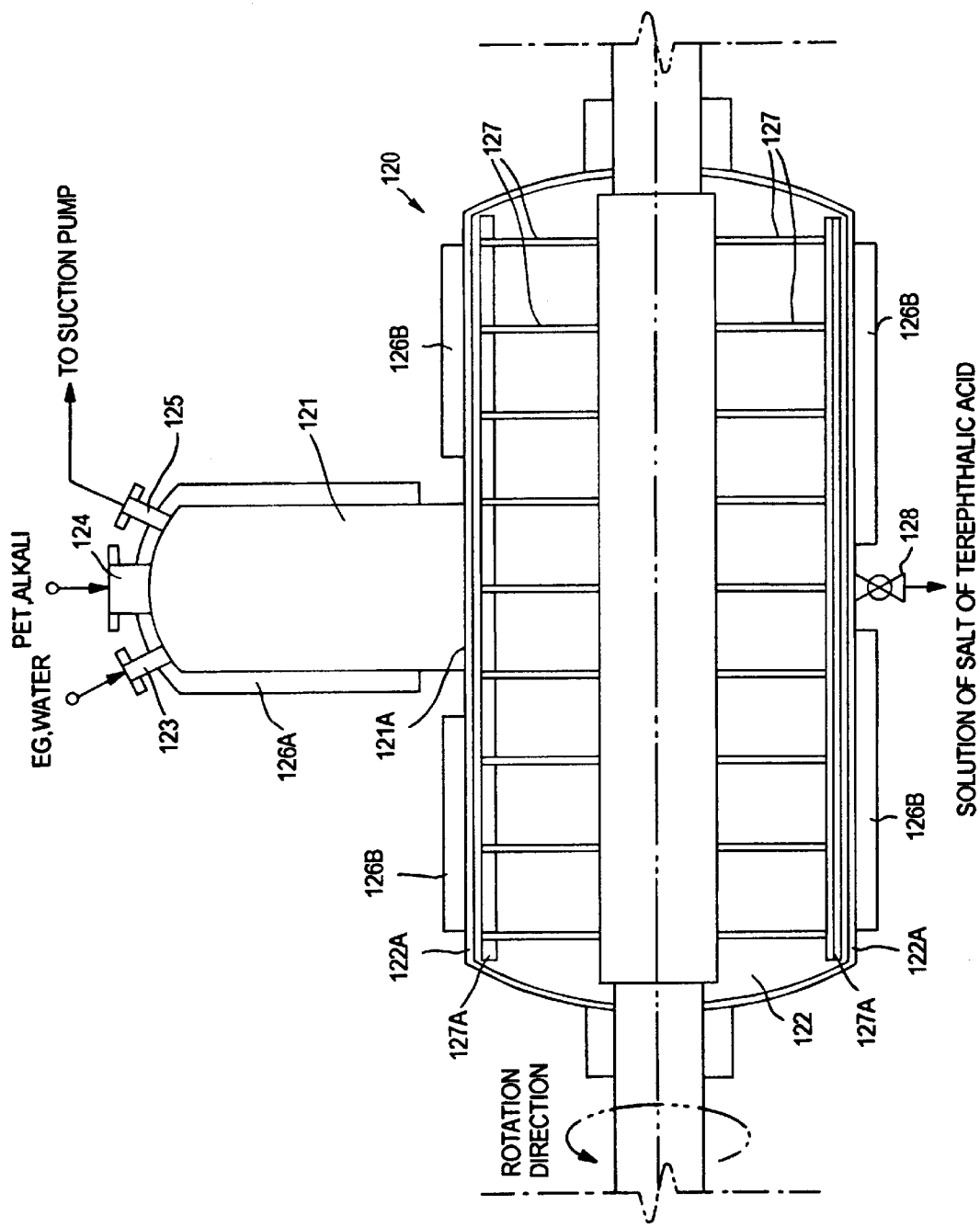
FIG. 15 is a simplified longitudinal sectional view of a decomposition vaporizing dissolver in the first embodiment in accordance with the fifth aspect of the present invention.
Figure 16:
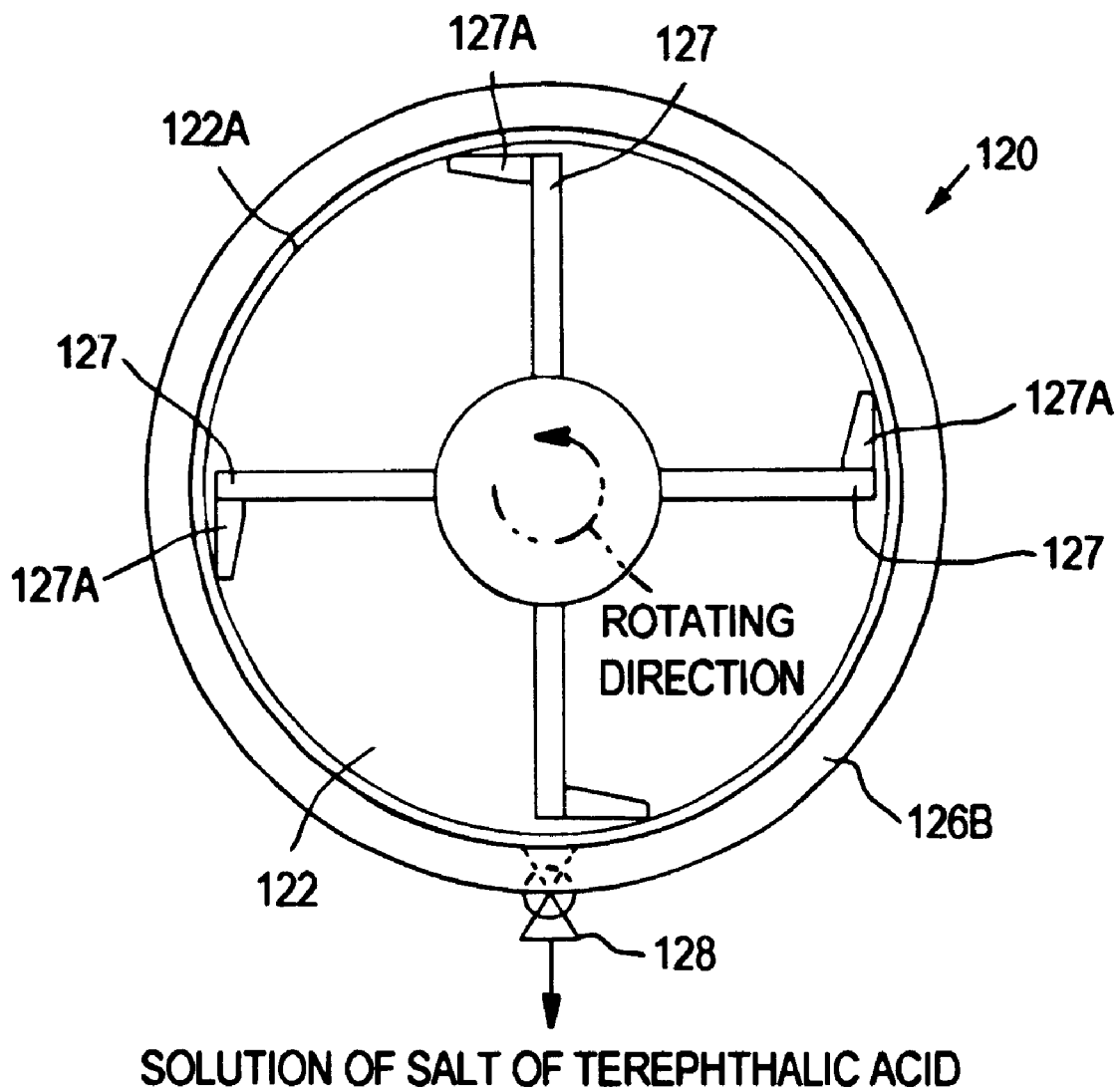
FIG. 16 is a simplified transverse sectional view of a decomposition vaporizing dissolver in the first embodiment in accordance with the fifth aspect of the present invention.

The First Embodiment in Accordance with the Fifth Aspect of the Present Invention FIGS. 15 and 16 show the first embodiment in accordance with the fifth aspect of the present invention. In this embodiment, from the beginning to producing of the solution of salt of terephthalate, operation is carried out with only a decomposition, separating dissolver 120.

The decomposition, separating dissolver 120 comprises a vacuum chamber 121 and a horizontal type decomposition reactor 122, which is communicated with the bottom surface of the vacuum chamber 21 and which has an axis along the horizontal direction. The vacuum chamber 121 is equipped with a charge inlet 124, through which the pulverized products of spent PET and alkali are charged into the vacuum chamber 121. The vacuum chamber 121 is also equipped with a charge inlet 123, through which the solvent (EG) and water for dissolving the solid salt of terephthalic acid are charged into the vacuum chamber 121. Then, the vacuum chamber 21 is equipped with a suction inlet 125, which is communicated with an evacuator (not shown) such as vacuum pump. Further, the decomposition reactor 122 is equipped, on the external surface of its peripheral portion 122A, with heating means, in this embodiment, jacket 126B, through which heat medium is passed. Then in the decomposition reactor 122, an agitating blade 127 is provided, which has an axis along the direction of the axis of the decomposition reactor 122 and which is extended to the internal surface of the peripheral portion 122A. Additionally, the vacuum chamber 121 is equipped with heating means, in this embodiment a jacket 126A, through which heat medium is passed, on the external surface of the peripheral portion.

In the decomposition, separating dissolver 120, first, through the charge inlet 123, the EG (solvent) is charged into the vacuum chamber 121. The charged EG is passed through the bottom surface 121A and gathered in the decomposition reactor 122. Then, the gathered EG is heated to the temperature of 120 to 190° C., in this embodiment to the temperature of 180° C. by the jacket 126B. After EG is heated, the pulverized products of spent PET and alkali are charged through the charge inlet 124. The ingredients are stirred by the agitating blade 127. Thus, the pulverized products of spent PET is subjected to decomposition reaction so that the terephthalic acid and EG are obtained (decomposition reaction step).

As stated before, if carbonate such as sodium carbonate is used as this charged alkali, carbon dioxide is generated the moment the decomposition reaction is started. Therefore, inert gas (such as nitrogen) is not required.

Even after the decomposition reaction is finished, the heated temperature must be kept and stirring operation must be also kept, in this embodiment, stirring with the agitating blade 127 is continued. In this situation, evacuating is carried out from the suction inlet 125 with the evacuator (not shown) so that inside of the decomposition separating dissolver 120 (i.e., inside of vacuum chamber 121 and decomposition reactor 122) is reduced to a vacuum. By doing so, the EG is vaporized and this steam is discharged through the suction inlet 125 from the vacuum chamber. Therefore, solid salt of terephthalic acid is remained in the decomposition reactor 122 (solid-liquid separation step). In this case, it is preferable that the EG is vaporized until the amount of the EG contained in the solid salt of terephthalic acid is decreased to 20 to 30% by mass thereof.

In the solid-liquid separation step, the solid salt of terephthalic acid can be attached to internal surface of the peripheral portion 122A of the reaction chamber 122. However, in this embodiment, the agitating blade 27 is extended to the internal surface of the peripheral portion 122A of the decomposition reactor 122. Particularly, a scraper 127A is equipped to the agitating blade 127 at its tip end. Therefore, such problem is not caused.

After the vaporization of EG is finished, the water is used 3 to 5 times as much as the solid salt of terephthalic acid for charging through the charge inlet 123 into the decomposition separating dissolver 120. In the dissolver, the solid salt of terephthalic acid is dissolved into the water (dissolution step). In this case, if the inside of the decomposition reactor 122 is heated to the temperature of about 90° C., dissolution can be performed easily.

The solution of salt of terephthalic acid generated from this dissolving operation is discharged through a valve 128 from the decomposition separating dissolver 120 and passed to the next step. After this, operation is continued in the same way as the treatment stated referring to FIG. 1.

Figure 17:
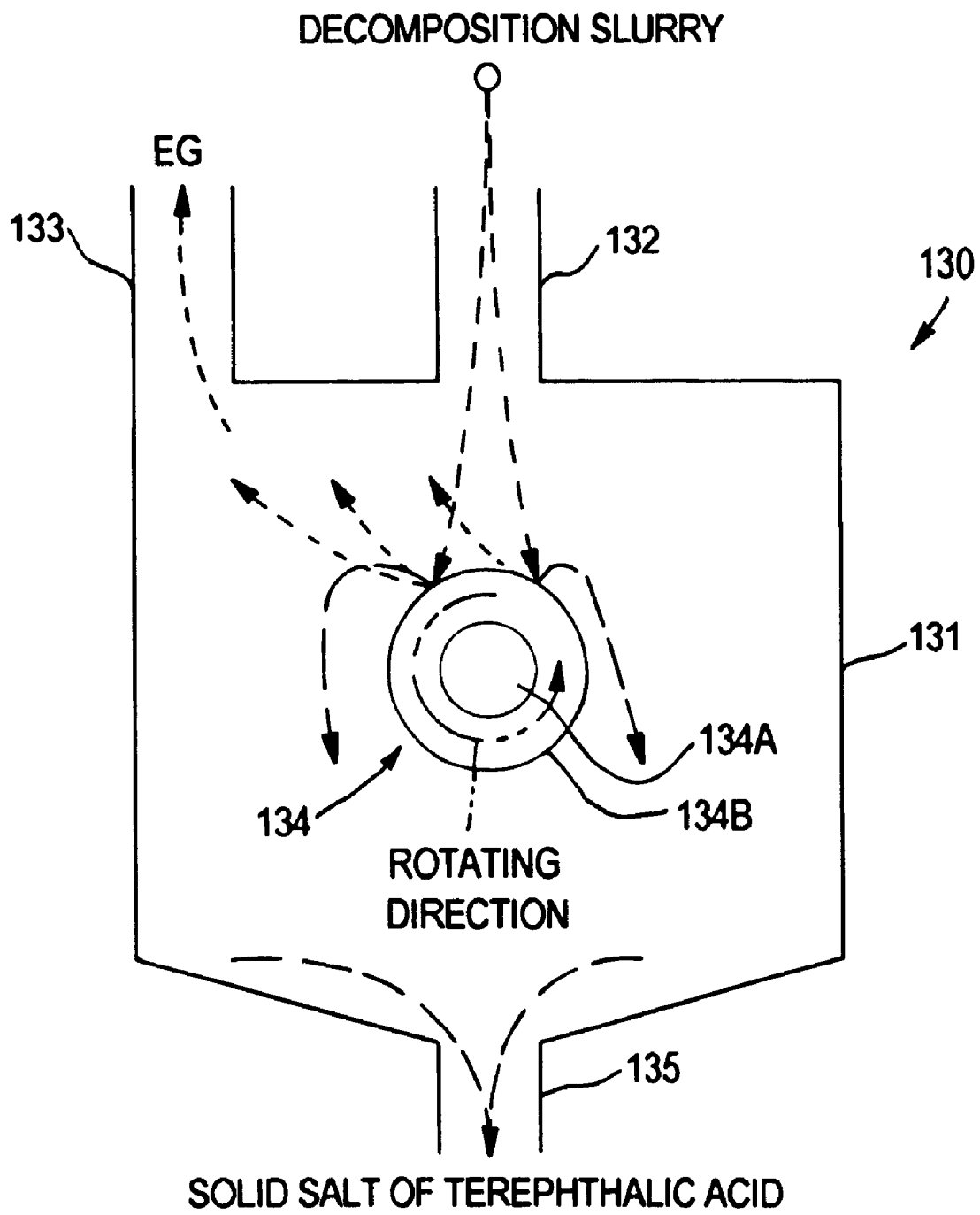
FIG. 17 is a simplified illustration of a solvent-removing apparatus in the second embodiment in accordance with the fifth aspect of the present invention.

The Second Embodiment in Accordance with the Fifth Aspect of the Present Invention FIG. 17 shows the second embodiment in accordance with the fifth aspect of the present invention. In this embodiment to perform the solid-liquid separation of salt of terephthalic acid and EG in the first aspect of the present invention, instead of solid-liquid separation and instead of centrifugal separator, a solvent-removing apparatus 130 is used.

The solvent-removing apparatus 130 has an evaporation can 131, which is equipped with a charge inlet 132, through which thermal cracking slurry generated from a decomposition reaction step (apparatus) is charged and a solvent-discharge outlet 133, through which removed solvent (in this embodiment, EG) and a monomer component, i.e., EG generated from the pulverized products of spent PET are discharged. The thermal cracking slurry is fallen through the charge inlet 132 into the evaporation can 130 by means of falling means (not shown). Then, in the body portion 131, a cylindrical rotating roll 134 is provided so that the fallen slurry can be brought into contact with the roll 134. The cylindrical roll 134 has a heating surface 134B, which is heated by heat medium 134A in a shaft of the roller to the temperature equal to or higher than the boiling point of the solvent. Particularly, in this embodiment, EG is used as the solvent, the temperature of the heating surface 134B is 200° C. or higher.

In the solvent-removing apparatus 130, first the thermal cracking slurry is fallen through the charge inlet 132 into the evaporation can 131 by means of the falling means. The fallen thermal cracking slurry is brought into contact with the rotating roll 134. The rotating roll 134 is rotated around the shaft and has the heating surface 134B, which is equal to or higher than the boiling point of the solvent. Therefore, the solvent is vaporized the moment it is brought into contact with the rotating roll 134. The heating surface might be plane-shaped, instead of roll-shaped. However, it is preferable that the heating surface is roll-shaped, because the temperature can be kept to be constant by rotating. The steam obtained from the EG can be recovered and returned to the decomposition reaction step (apparatus). Further, by adjusting the rotation speed of the rotating roller 134 and the temperature of the heating surface 134B, the amount of evaporated EG can be controlled.

By the vaporization of EG, the thermal cracking slurry becomes to solid containing mainly the solid salt of terephthalic acid, which is dropped downward to the lower portion of the evaporation can 131. Thus dropped solid is discharged through the discharge outlet 135 from the evaporation can 131 and passed to a dissolution step. After this, operation is continued in the same way as stated before.

As for the thermal cracking slurry, instead of being passed to the dissolution step as the solid salt of terephthalic acid, water is supplied into the body portion 131, when the solid salt of terephthalic acid is dissolved into the water for obtaining the solution of the salt of terephthalic acid.

Example 5

A vertical type cylindrical stirrer, which has the size of 150 mm diameter by 200 mm height and which is equipped with a heating jacket on its external periphery is filled with 1800 g of EG and it is heated to the temperature of 180° C. Next, 600 g of the pulverized products of spent PET each having the shape of 6 to 8 mm square and 360 g of sodium carbonate are charged into the vertical type cylindrical stirrer. Then, the ingredients are stirred for 30 minutes.

Then, the inside of the vertical type cylindrical stirrer is reduced to 100 mm Hg by means of a vacuum pump and the ingredients are stirred for 30 minutes so that EG is vaporized. Then, solid is obtained The amount of EG contained in the solid is 20 mass percent.

Next, water is fed 5 times as much as the solid into the vertical type cylindrical stirrer so that solution of salt of terephthalic acid is obtained. This solution of salt of terephthalic acid is filtered a sloping screen for removing insoluble impurities such as unreacted PET, PP and PE. As a result, 18 g of PET is not unreacted. 97% of PET is reacted.

The First Embodiment in Accordance with the Sixth Aspect of the Present Invention Now, the first embodiment in accordance with the sixth aspect of the present invention will be explained. In the sixth aspect of the present invention, in the neutralization, crystallization step stated before, acid is added in multiple stages. Particularly, in this embodiment, acid is added in two stages and the pH value of solution in the second neutralization step is adjusted so as to be 2 to 4. Further, the solution in the second neutralization step is passed into a classifier, where terephthalic acid crystals each having the particle size of predetermined value or smaller are classified. Thus classified terephthalic acid crystals are returned to the solution of the first neutralization stage for dissolving.

Figure 18:
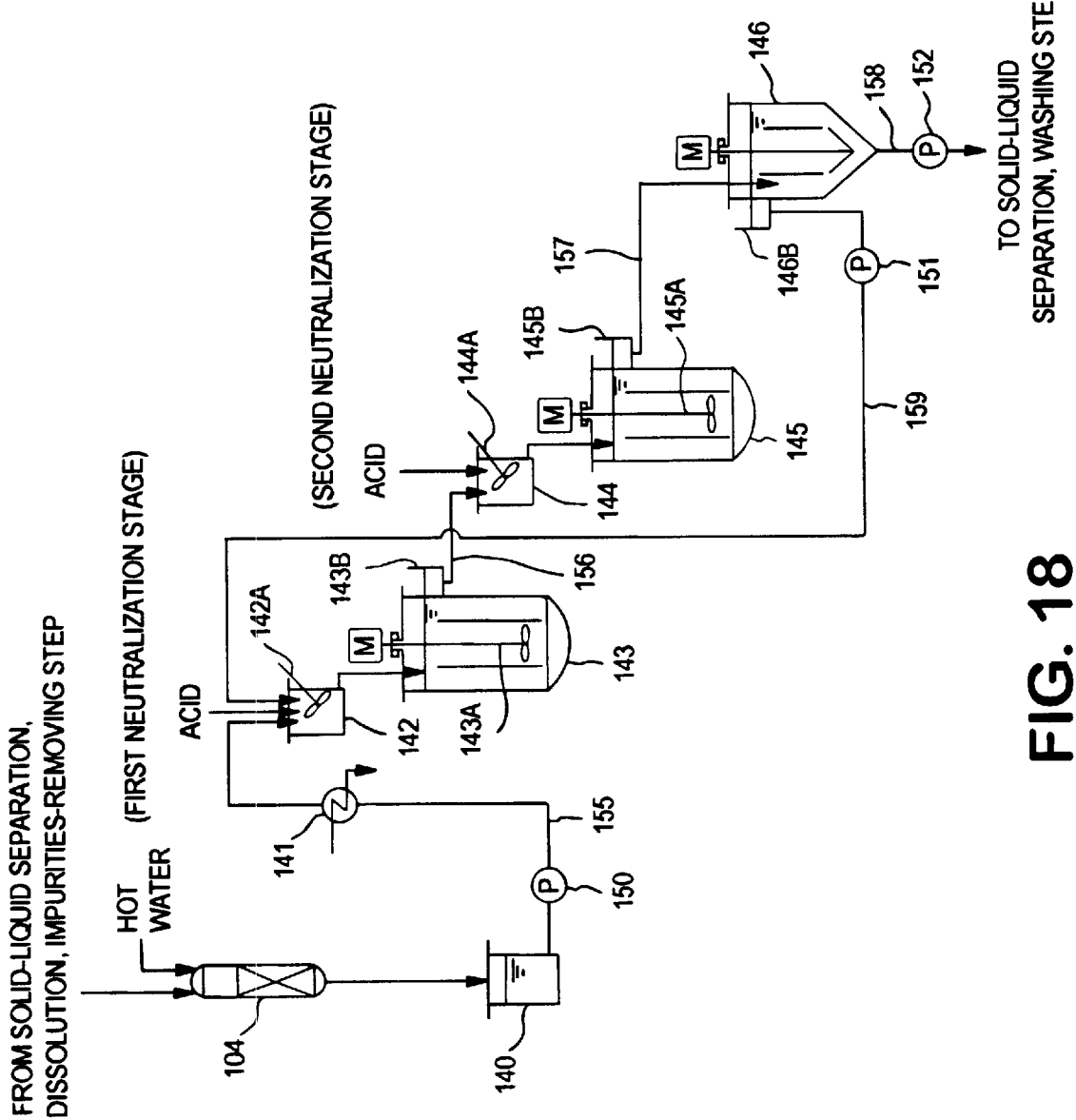
FIG. 18 is a flow sheet of neutralization in the first embodiment in accordance with the sixth aspect of the present invention.

Concretely, in the embodiment shown in FIG. 18, a pot 142 and a neutralization chamber 143 are provided.for the neutralization of the first stage (the first neutralization stage). On the other hand, a pot 144 and a neutralization chamber 145 are provided for the neutralization of the second stage (the second neutralization stage). Finally, a classifier 146 is provided for classifying the terephthalic acid crystals each having the particle size of predetermined value or smaller.

First, the solution of salt of terephthalic acid generated from the solid-liquid separation, dissolution, impurities-removing step, is passed to a impurities-removing apparatus, in this embodiment vertical type adsorptive active carbon packed cylindrical column 104. Before this, operation is carried out in the same way as stated above. Then, this solution is gathered temporally at a solution of salt of terephthalic acid reservoir 140. The gathered solution of salt of terephthalic acid is passed through a transport pipe 155 and is heated to the temperature of 95° C. by a heat exchanger 141 equipped to the transport pipe 155 to the pot 142 by means of a plump 150. The pot 142 is provided at the upstream-side of the neutralization chamber 143. In the chamber 143, there is provided a stirrer 142A. As the pot, apparatus shown in FIG. 4 can be used. This alternative apparatus serves as the neutralization chamber in the embodiment shown in FIG. 1. In the pot 142, to the solution of salt of terephthalic acid obtained from the reservoir 140, acid such as sulfuric acid is added and solution of terephthalic acid fine crystals (stated below) generated from the classifier 146 is mixed, and the ingredients are stirred with the stirrer 142A. The resulting solution of salt of terephthalic acid is further passed to the neutralization chamber 143, where it is stirred with a stirrer 143A (the first neutralization stage).

In the first neutralization stage, the acid is added so that terephthalic acid is not crystallized in the neutralization chamber 143, for example, so that the pH value of the solution in the neutralization chamber 143 can be adjusted to 6. In this stage, alkali, which was added in the thermal cracking step, is neutralized so as to be alkali salt.

After the neutralization of the solution of salt of terephthalic acid in the neutralization chamber 143, this solution is discharged from the upper portion 143B of the peripheral of the neutralization chamber 143, and passed through a transport pipe 156 to a pot 144, which is configured in the same way as the pot 142.

In the pot 144, to the solution of salt of terephthalic acid obtained from the neutralization chamber 143, acid such as sulfuric acid is added, and the ingredients are stirred with the stirrer 144A. The resulting solution of salt of terephthalic acid is further passed to a neutralization chamber 145, which is configured in the same way as the neutralization chamber 143 and in which, it is stirred with a stirrer 145A (the second neutralization stage).

In the second neutralization stage, the acid is added so that terephthalic acid is crystallized from the solution in the neutralization chamber 145, for example, so that the pH value of the solution in the neutralization chamber 145 can be adjusted to 2 to 4.

The resulting solution, in which the terephthalic acid crystals were contained, is discharged from the upper portion 145B of the peripheral side of the neutralization chamber 145, and passed through a transport pipe 157 to a classifier 146.

From the classifier 146, supernatant liquid stayed in the predetermined range of level, i.e., solution containing the terephthalic acid crystals each having the particle size of predetermined value and smaller (terephthalic acid fine crystals) is discharged through an upper portion 146B of peripheral side of the classifier 146, and passed through a transport pipe 159 for returning to the pot 142 by means of a pump 151. By doing so, the particle size of terephthalic acid crystal can be increased (average particle size) uniformly.

After the supernatant liquid is returned, the solution of terephthalic acid contained in the classifier 146 is discharged from its bottom and passed through a transport pipe 158 to a solid-liquid separation, washing step. After this, operation is carried out in the same way as the basic embodiment.

Figure 19:
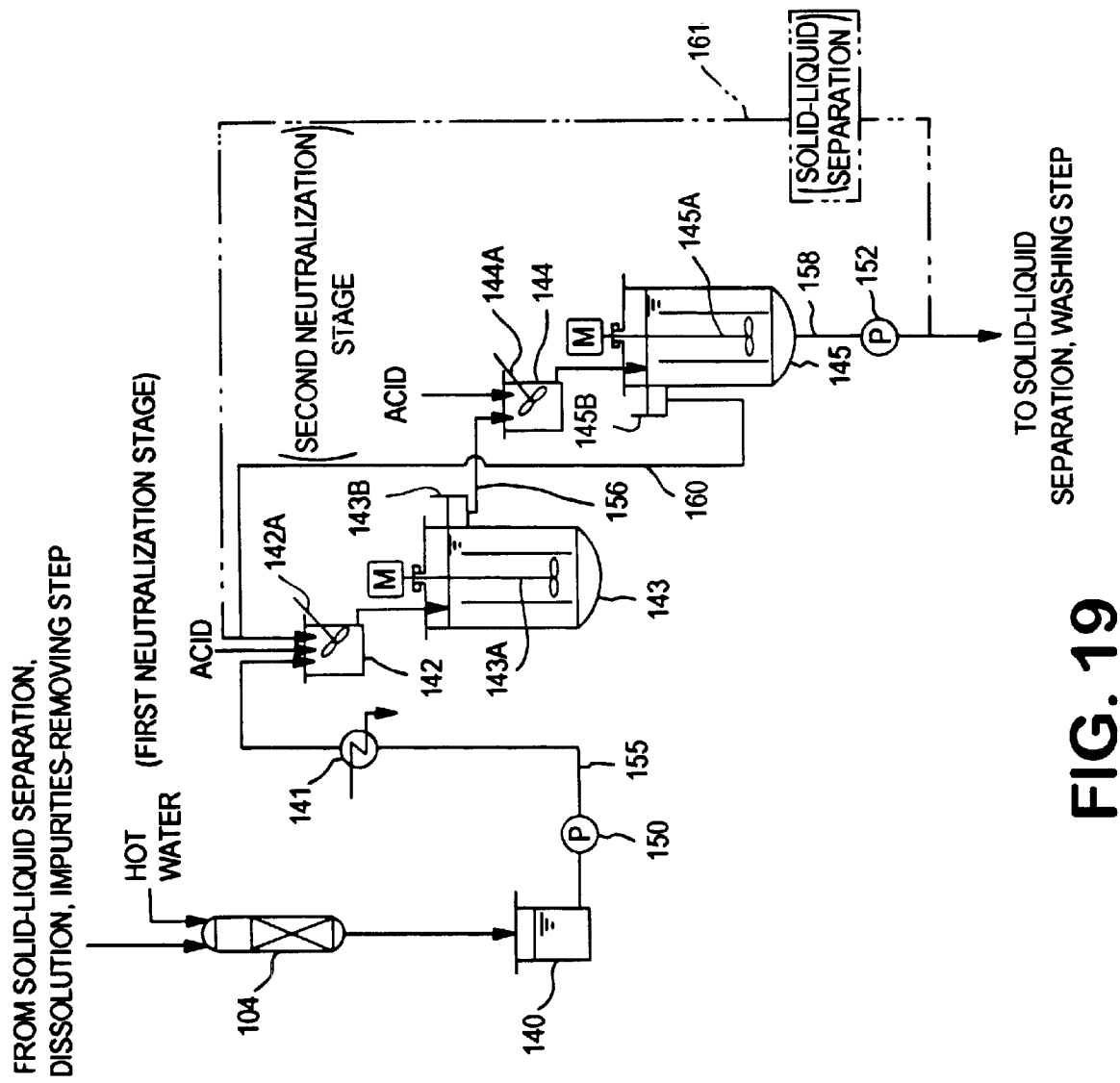
FIG. 19 is a flow sheet of neutralization in the second embodiment in accordance with the sixth aspect of the present invention.

The Second Embodiment in Accordance with the Sixth Aspect of the Present Invention FIG. 19 shows the second embodiment in accordance with the sixth aspect of the present invention. This second embodiment has the same construction as the first embodiment except difference in treatment after the neutralization. In the second embodiment, solution, which contain terephthalic acid crystals due to neutralization in a neutralization chamber 145, is divided into two parts; upper layer part and lower layer part. The solution stayed in the upper layer part (solution containing terephthalic acid fine crystals) is discharged from the upper portion 145B of the peripheral side of the neutralization chamber 145, and returned through a transport pipe 160 to the pot 142. On the other hand, the solution stayed in the lower layer part (solution containing terephthalic acid crystals each having comparatively large particle size) is discharged from the bottom of the neutralization chamber 145. Thus discharged solution is partly passed through a transport pipe 158 to a solid-liquid separation step by means of a pump 152. Then the reminder is, separated into terephthalic acid crystals and water or the like if desired, and the terephthalic acid crystals are returned through a transport pipe 161 to the pot 142 for re-dissolution. By doing so, the purity of terephthalic acid crystal can be increased. Additionally, the particle size of each crystal can be further increased.

Example 6

Salt of terephthalic acid generated from the thermal cracking of the pulverized products of spent PET is dissolved into water so that solution of salt of terephthalic acid can be obtained. Then, insoluble impurities are removed with a filter and soluble impurities are removed with active carbons, The solution from which the impurities are removed contains 10 mass % of salt of terephthalic acid, 10 mass % of EG and 20 mass % of alkali. Next, this solution is heated to the temperature of 95° C. Then, this heated solution is continuously charged into the first reactor glass beaker equipped with a stirrer) having the size of 200 mm diameter by 300 mm height with the flow rate of 60 kg/Hr. To the first reactor, solution of terephthalic acid generated from a classifier stated below is also continuously charged with the flow rate of 60 kg/Hr. Further, to the first reactor, 4N sulfuric acid is continuously added so that the pH value of the solution is adjusted to 6. In the first reactor, terephthalic acid is not crystallized (the first neutralization stage).

Solution of salt of terephthalic acid is continuously discharged from the above first neutralization stage and is continuously charged into the second reactor (glass beaker equipped with a stirrer) having the size of 200 mm diameter by 300 mm height. To the second reactor, 4N sulfuric acid is continuously added so that the pH value of the solution is adjusted to 3. Finally, terephthalic acid is crystallized (the second neutralization stage).

The solution of terephthalic acid obtained from the second reactor is passed to the classifier where the solution is classified. Then, the supernatant liquid in the classifier is returned to the solution in the first neutralization stage.

The remained solution of terephthalic acid is passed through filtration, washing, drying step, so that dried terephthalic acid is obtained. The average particle size is 30 $\mu$m and purity is 99.9%.

What is claimed is:

1. A process for recovering terephthalic acid from pulverized products of spent polyethylene terephthalate, the process comprising the following steps:

(1) a decomposition reaction step where the pulverized products of spent polyethylene terephthalate are continuously subjected to a decomposition reaction in ethylene glycol in the presence of sodium carbonate, which is equimolar or excessmolar relative to the polyethylene terephthalate, so that a salt of terephthalic acid and ethylene glycol can be obtained;

(2) a solid-liquid separation, dissolution, impurities-removing step where said ethylene glycol is separated from the decomposition reaction slurry of said salt of terephthalic acid and ethylene glycol, and the solid salt of terephthalic acid is dissolved into water, and insoluble impurities are removed;

(3) a neutralization, crystallization step, where the solution of said salt of terephthalic acid is neutralized with acid so that terephthalic acid can be crystallized;

(4) a solid-liquid separation washing step, where the resulting slurry of terephthalic acid crystals is subjected to solid-liquid separation, so that the terephthalic acid crystals can be obtained and washed;

(5) a drying, pulverization step, where the washed terephthalic acid crystals are dried and pulverized; and further comprising a condensation, crystallization, mirabilite-removing step, where water contained in the liquid obtained by said separation step (4) is vaporized, so that alkali sulfate can be crystallized and separated.

2. A process for recovering terephthalic acid from pulverized products of spent polyethylene terephthalate, the process comprising the following steps:

(1) a decomposition reaction step where the pulverized products of spent polyethylene terephthalate are continuously subjected to decomposition reaction in ethylene glycol in the presence of sodium carbonate, which is equimolar or excessmolar relative to the polyethylene terephthalate, so that a salt of terephthalic acid and ethylene glycol can be obtained;

(2) a solid-liquid separation, dissolution, impurities-removing step where said ethylene glycol is separated from the decomposition reaction slurry of said salt of terephthalic acid and ethylene glycol, and the solid salt of terephthalic acid is dissolved into water, and insoluble impurities are removed;

(3) a neutralization, crystallization step, where the solution of said salt of terephthalic acid is neutralized with acid so that terephthalic acid can be crystallized;

(4) a solid-liquid separation, washing step, where the resulting slurry of terephthalic acid crystals is subjected to solid-liquid separation so that the terephthalic acid crystals can be obtained and washed;

(5) a drying, pulverization step where the washed terephthalic acid crystals are dried and pulverized; and further comprising following steps:

(6) a return step where said ethylene glycol, which is obtained by the solid-liquid separation in said step (2), is returned to said step (1); and (7) a vaporization, crystallization, separation, return step, where water contained in the liquid, which is obtained by solid-liquid separation of said step (4) and which contains salt, water and ethylene glycol, is vaporized so that said salt can be crystallized and separated, then the ethylene glycol is returned to said step (1).

3. A process for recovering terephthalic acid from pulverized products of spent polyethylene terephthalate, the process comprising the following steps:

(1) a decomposition reaction step where the pulverized products of spent polyethylene terephthalate are continuously subjected to decomposition reaction in ethylene glycol in the presence of sodium carbonate, which is equimolar or excessmolar relative to the polyethylene terephthalate, so that a salt of terephthalic acid and ethylene glycol can be obtained;

(2) a solid-liquid separation, dissolution impurities-removing step where said ethylene glycol is separated from the decomposition reaction slurry of said salt of terephthalic acid and ethylene glycol, and the solid salt of terephthalic acid is dissolved into water, and insoluble impurities are removed;

(3) a neutralization, crystallization step, where the solution of said salt of terephthalic acid is neutralized with acid so that terephthalic acid can be crystallized;

(4) a solid-liquid separation, washing step where the resulting slurry of terephthalic acid crystals is subjected to solid-liquid separation so that the terephthalic acid crystals can be obtained and washed;

(5) a drying, pulverization step where the washed terephthalic acid crystals are dried and pulverized; and further comprising the following step between said step (2) and step (3), (8) a soluble impurities-removing step, where soluble impurities contained in solution in said step (2) can be continuously removed with an adsorbent packed adsorber.

4. A process according to claim 2 or 3, wherein as water used for dissolution in said step (2), wash water of said adsorber used in said step (8) and/or condensate obtained by cooling steam in said step (7).

5. A process for recovering terephthalic acid from pulverized products of spent polyethylene terephthalate, the process comprising a decomposition reaction heating carried out for said pulverized products of spent polyethylene terephthalate in solvent in the presence of sodium carbonate, which is equimolar or excessmolar relative to the polyethylene terephthalate, so that a salt of terephthalic acid and ethylene glycol can be obtained, for recovering terephthalic acid from resulting salt of terephthalic acid, before said decomposition reaction, said pulverized products being subjected to thermal degradation; and wherein, heat generated by said pulverized products subjected to said thermal degradation is recycled for said decomposition reaction heating.

6. A process for recovering terephthalic acid from pulverized products of spent polyethylene terephthalate the process comprising: subjecting said pulverized products of spent polyethylene terephthalate to thermal cracking in the presence of sodium carbonate so that a salt of terephthalic acid and ethylene glycol can be obtained; removing said ethylene glycol from thermal cracking slurry so that a solid salt of terephthalic acid can be obtained; dissolving said solid salt of terephthalic acid into water so that a solution of salt of terephthalic acid can be obtained; neutralizing said solution of salt of terephthalic acid by adding acid so that terephthalic acid can be crystallized; and recovering said terephthalic acid and said acid being added in multiple stages, while the amount of added acid is determined so that the pH value of the solution in the final stage is adjusted to 2 to 4 and terephthalic acid crystals obtained from said final stage being returned to said previous stage for dissolving and wherein the amount of added acid is determined so as not to crystallize said terephthalic acid in a previous stage.

7. A process for recovering terephthalic acid from pulverized products of spent polyethylene terephthalate the process comprising: subjecting said pulverized products of spent polyethylene terephthalate to thermal cracking in the presence of sodium carbonate so that salt of terephthalic acid and ethylene glycol can be obtained; removing said ethylene glycol from thermal cracking slurry so that a solid salt of terephthalic acid can be obtained; dissolving said solid salt of terephthalic acid into water so that a solution of salt of terephthalic acid can be obtained; neutralizing said solution of salt of terephthalic acid by adding acid so that terephthalic acid can be crystallized; and recovering said terephthalic acid and said acid being added in multiple stages, while the amount of added acid is determined so that the pH value of the solution in the final stage is adjusted to 2 to 4 and terephthalic acid crystals obtained from said final stage being returned to said previous stage for dissolving and wherein solution containing said terephthalic acid crystals is subjected to solid-liquid separation so the that resulting terephthalic acid crystals are returned to said previous stage for being dissolved again.

* * * * *